(12) United States Patent
Zhu et al.

(10) Patent No.: US 12,312,373 B2
(45) Date of Patent: May 27, 2025

(54) CYCLOPROPANE SKELETON MONOPHOSPHINE LIGANDS, PALLADIUM COMPLEXES THEREOF, PREPARATION METHODS AND APPLICATION

(71) Applicant: Nankai University, Tianjin (CN)

(72) Inventors: Shoufei Zhu, Tianjin (CN); Huawei Liu, Tianjin (CN); Wei Sun, Tianjin (CN); Wentao Li, Tianjin (CN); Ling Dang, Tianjin (CN); Mingyao Huang, Tianjin (CN); Xinyu Zhang, Tianjin (CN)

(73) Assignee: Nankai University, Tianjin (CN)

( * ) Notice: Subject to any disclaimer, the term of this patent is extended or adjusted under 35 U.S.C. 154(b) by 0 days.

(21) Appl. No.: 18/783,334

(22) Filed: Jul. 24, 2024

(65) Prior Publication Data

US 2024/0376136 A1 Nov. 14, 2024

Related U.S. Application Data

(63) Continuation of application No. PCT/CN2022/138338, filed on Dec. 12, 2022.

(30) Foreign Application Priority Data

Jan. 26, 2022 (CN) .......................... 202210095869.3

(51) Int. Cl.
| | | |
|---|---|---|
| C07D 209/08 | (2006.01) | |
| B01J 31/24 | (2006.01) | |
| C07C 209/60 | (2006.01) | |
| C07C 213/00 | (2006.01) | |
| C07C 253/30 | (2006.01) | |
| C07D 279/22 | (2006.01) | |
| C07F 9/50 | (2006.01) | |
| C07F 15/00 | (2006.01) | |

(52) U.S. Cl.
CPC ............ *C07F 9/5018* (2013.01); *B01J 31/24* (2013.01); *C07C 209/60* (2013.01); *C07C 213/00* (2013.01); *C07C 253/30* (2013.01); *C07D 209/08* (2013.01); *C07D 279/22* (2013.01); *C07F 9/5068* (2013.01); *C07F 15/0066* (2013.01)

(58) Field of Classification Search
CPC .................................................. C07D 209/08
See application file for complete search history.

(56) References Cited

FOREIGN PATENT DOCUMENTS

CN 111018923 A 4/2020

OTHER PUBLICATIONS

American Chemical Society. Chemical Abstract Service. RN 39980-48-8. Entered into STN: Nov. 16, 1984. (Year: 1984).*
"Installation of protected ammonia equivalents onto aromatic & heteroaromatic rings in water enabled by micellar catalysis" Green Chemistry; Isley Nicholas A et al.; vol. 16, Issue 3, Jan. 2, 2014 (Jan. 2, 2014), ISSN: 1463-9262. pp. 1480-1488, p. 1480, right column, paragraph 3; claims 1-3.
"Insights on Bimetallic Micellar Nanocatalysis for Buchwald-Hartwig Aminations" ACS Catalysis, Ansari Tharique N. et al.; vol. 9, Issue 11, Sep. 17, 2019 (Sep. 17, 2019), ISSN:2155-5435.pp. 10389-10397, para. 2, left-hand column, p. 10390; claims 1-10.
"BuchwaldeHartwig reactions in water using surfactants" Tetrahedron; SAL0ME Christophe et al.; vol. 70, Issue 21, Apr. 1, 2014 (Apr. 1, 2014), ISSN:0040-4020. 3413-3421, p. 3414, left-hand column, paragraph 1; claims 1-3.
"Synthesis of Well-Defined Diphenylvinyl(cyclopropyl)phosphine-Palladium Complexes for the Suzuki-Miyaura Reaction and Buchwald-Hartwig Amination" Advanced Synthesis &Catalysis, Naota Yokoyama et al.; vol. 355, Issue 10, Jul. 12, 2013 (Jul. 12, 2013),ISSN: 1615-4150, pp. 2083-2088, para. 1, left-hand column, p. 2083, para. 2, right-hand column, p. 2087; claims 1-3, 7-10.
"A New Hybrid Phosphine Ligand for Palladium-Catalyzed Amination of Aryl Halides" Advanced Synthesis & Catalysis, Suzuki Ken et al.; vol. 350, Issue 5, Mar. 17, 2008 (Mar. 17, 2008)ISSN:1615-4150.pp. 652-656, Figure 2, p. 652, para. 3, left column, p. 655; claims 1-6.

* cited by examiner

*Primary Examiner* — John S Kenyon

(57) ABSTRACT

The present invention relates to cyclopropane skeleton monophosphine ligands and preparation methods for palladium complexes thereof and an application. Specifically, trans-diaryl substituted cyclopropane skeleton monophosphine ligands are synthesized after trans-1,2-diaryl ethylene undergoing the steps of cyclopropanation reaction, debromination reaction, substitution reaction, and the like. Palladium complexes prepared by coordinating the cyclopropane skeleton monophosphine ligands with a palladium salt show very high activity in catalyzing C—N bond coupling reactions, and have good application prospects.

6 Claims, 2 Drawing Sheets

CYCLOPROPANE SKELETON MONOPHOSPHINE LIGANDS, PALLADIUM COMPLEXES THEREOF, PREPARATION METHODS AND APPLICATION

CROSS-REFERENCE TO RELATED APPLICATIONS

This application is a continuation of PCT/CN2022/138338, filed Dec. 12, 2022 and claims priority of Chinese Patent Application No. 202210095869.3, filed on Jan. 26, 2022, the entire contents of which are incorporated herein by reference.

TECHNICAL FIELD

The present invention relates to cyclopropane skeleton monophosphine ligands, palladium complexes thereof, preparation methods and an application. Specifically, trans-diaryl substituted cyclopropane skeleton monophosphine ligands are synthesized after trans-1,2-diaryl ethylene undergoing the steps of cyclopropanation reaction, debromination reaction, substitution reaction, and the like. Palladium complexes are prepared by coordinating the cyclopropane skeleton monophosphine ligands with palladium salts show very high activity in catalyzing C—N bond coupling reactions and have good application prospects.

BACKGROUND

The Buchwald-Hartwig reaction refers to the palladium-catalyzed C—N cross-coupling reaction of aryl electrophilic reagents with amines and is widely applied in the synthesis of pharmaceuticals, natural products, and functional materials [(1) Ruiz-Castillo, P.; Buchwald, S. L. Chem. Rev. 2016, 116, 12564. (2) Surry, D. S.; Buchwald, S. L. Chem. Sci. 2011, 2, 27.]. In this reaction, ligands can affect the activity and selectivity of a catalyst by modulating the electrical properties and steric hindrance of the palladium center, so the design and synthesis of ligands are the core research focus of the Buchwald-Hartwig reaction.

In the past two decades or so, the design and synthesis of ligands have greatly contributed to the advancement of C—N bond coupling, and the series of biarylphosphine ligands designed by Buchwald's research group are most representative, realizing the efficient coupling of primary amines (Brettphos and Gphos), secondary amines (RuPhos), amines containing large steric hindrance substituents ('BuPhCPhos), and heterocyclic amines (EPhos). Although the Buchwald-Hartwig reaction has been well developed, most of these reactions require large amounts of palladium catalyst (1 mol % or more), with turnover numbers (amount of substance of product/amount of substance of palladium catalyst) of less than 100, which results in high synthesis costs on the one hand and poses the problem of heavy metal residues on the other hand, affecting the wider application of this reaction in the pharmaceutical field. Taking the C—N bond coupling of diarylamines to aryl halides as an example, there are only a few catalysts can generate turnover numbers of 1000 or more, including complexes of P'Bu$_3$ and palladium can generate as high as 3960 turnover numbers [Yamamoto, T.; Nishiyama, M.; Koie, Y. Tetrahedron Lett. 1998, 39, 2367.], complexes of RuPhos and palladium can generate as high as 1980 turnover numbers [Fors, B. P.; Buchwald, S. L. J. Am. Chem. Soc. 2010, 132, 15914.], and complexes of Cy-vBRIDP and palladium can generate as high as 1980 turnover numbers [Nkayama, Y. Yokoyama, N.; Nara, H.; Kobayashi, T.; Fujiwhara, M. Adv. Synth. Catal. 2015, 357, 2322.]. Therefore, improving the activity of the Buchwald-Hartwig reaction and reducing the amount of palladium catalyst by designing and synthesizing new phosphine ligands is one of the research focuses in this field, which has important theoretical and practical significance.

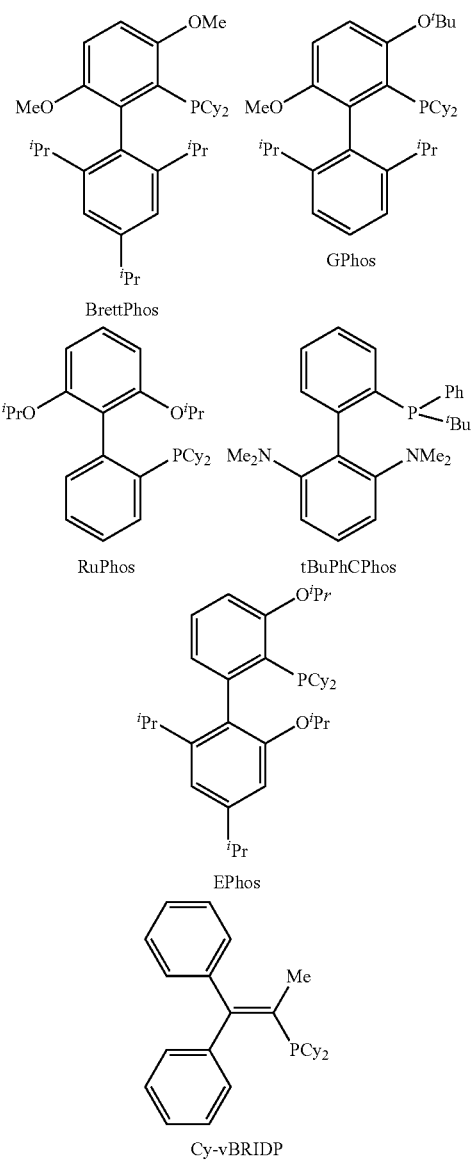

SUMMARY

An objective of the present invention is to provide cyclopropane skeleton monophosphine ligands and a preparation method therefor, to overcome the shortcomings in the prior art.

Another objective of the present invention is to provide adducts of the cyclopropane skeleton monophosphine ligands and borane and a preparation method therefor.

Another objective of the present invention is to provide complexes of the cyclopropane skeleton monophosphine ligands with palladium and preparation methods therefor.

Another objective of the present invention is to provide an application of the complexes of the cyclopropane skeleton monophosphine ligands with palladium as catalysts in promoting a Buchwald-Hartwig reaction.

Cyclopropane skeleton monophosphine ligands have the following structural formula as I or an enantiomer and a racemate of the following structural formula as I:

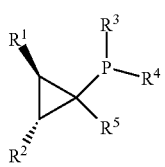

I where $R^1$ and $R^2$ are phenyl or substituted phenyl, $R^3$ and $R^4$ are phenyl, substituted phenyl, or $C_1$-$C_8$ alkyl, and $R^5$ is a hydrogen atom, phenyl, substituted phenyl, or $C_1$-$C_8$ alkyl, $R^1$, $R^2$, $R^3$, $R^4$, and $R^5$ being same or different.

In the substituted phenyl, a substituent is one or more of $C_1$-$C_8$ alkyl, $C_1$-$C_8$ alkoxy, $C_2$-$C_8$ acyloxy, hydroxy, halogen, amino, ($C_1$-$C_8$ acyl) amino, bis ($C_1$-$C_8$ alkyl) amino, $C_1$-$C_8$ acyl, $C_2$-$C_8$ ester, or haloalkyl. If $R^1$ and $R^2$ are substituted phenyl, the number of substituents is 0-2; and if $R^3$ and $R^4$ are substituted phenyl, the number of substituents is 0-5.

In the above technical solution, in the cyclopropane skeleton monophosphine ligands, alkyl in the $C_1$-$C_8$ alkyl or in the $C_1$-$C_8$ alkoxy is methyl, ethyl, n-propyl, isopropyl, cyclopropyl, n-butyl, isobutyl, sec-butyl, tert-butyl, n-amyl, isopentyl, neopentyl, sec-pentyl, tert-pentyl, n-hexyl, isohexyl, neohexyl, sec-hexyl, tert-hexyl, n-heptyl, isoheptyl, neoheptyl, sec-heptyl, tert-heptyl, n-octyl, isooctyl, neooctyl, sec-octyl, or tert-octyl;

the $C_1$-$C_8$ acyl is formyl, acetyl, propionyl, n-butyryl, isobutyryl, n-valeryl, isovaleryl, sec-valeryl, pivaloyl, n-hexanoyl, isocaproyl, neocaproyl, sec-caproyl, n-heptanoyl, isoheptanoyl, neoheptanoyl, sec-heptanoyl, n-octanoyl, isooctanoyl, neooctanoyl, sec-octanoyl, 1-cyclopropylformyl, 1-cyclobutylformyl, 1-cycloamylformyl, 1-cyclohexylformyl or 1-cycloheptylformyl;

the $C_2$-$C_8$ acyloxy is acetoxy, propionyloxy, n-butyloxy, isobutyloxy, n-valeroyloxy, isovaleroyloxy, sec-valeroyloxy, neovaleroylox, n-hexanoyloxy, isohexanoyloxy, neohexanoyloxy, sec-hexanoyloxy, n-heptanoyloxy, isoheptanoyloxy, neoheptanoyloxy, sec-heptanoyloxy, n-octanoyloxy, isooctanoyloxy, neooctanoyloxy, sec-octanoyloxy, 1-cyclopropylformyloxy, 1-cyclobutylformyloxy, 1-cyclopentylformyloxy, 1-cyclohexylformyloxy or 1-cycloheptylformyloxy;

the $C_2$-$C_8$ ester is methoxycarbonyl, ethoxycarbonyl, propoxycarbonyl, isopropoxycarbonyl, butoxycarbonyl, isobutyloxycarbonyl, n-pentoxycarbonyl, isopentoxycarbonyl, neopentoxycarbonyl, sec-pentoxycarbonyl, tert-pentoxycarbonyl, cyclopentoxycarbonyl, n-hexyloxycarbonyl, isohexyloxycarbonyl, neohexyloxycarbonyl, sec-hexyloxycarbonyl, tert-hexyloxycarbonyl, cyclohexyloxycarbonyl, n-heptyloxycarbonyl, isoheptyloxycarbonyl, neoheptyloxycarbonyl, sec-heptyloxycarbonyl, tert-heptyloxycarbonyl, or cycloheptyloxycarbonyl; and the haloalkyl is fluorine-, chlorine-, bromine- or iodine-containing haloalkyl.

In the above technical solution, the cyclopropane skeleton monophosphine ligands have the following structural formulas as I-a, I-b, I-c, I-d, I-e, I-f, or I-g:

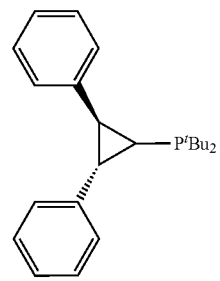

I-a

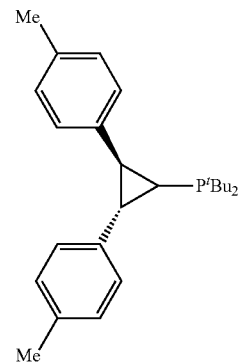

I-b

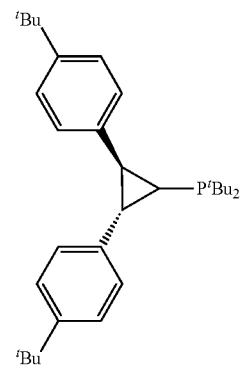

I-c

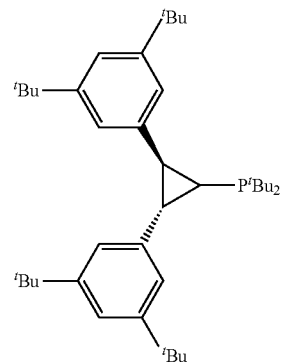

I-d

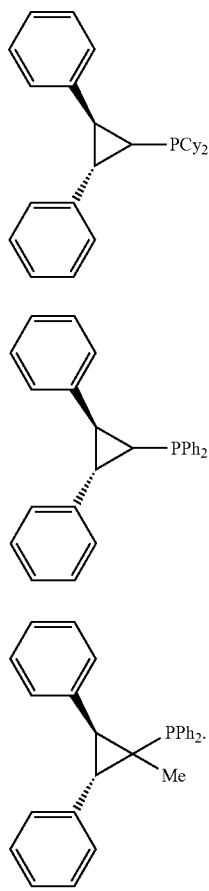

In another aspect of the present invention, a preparation method for cyclopropane skeleton monophosphine ligands includes the following two routes.

When $R^5$ =H, a synthetic route is as follows. In the presence of NaOH and a phase transfer catalyst benzyltriethylammonium chloride (TEBAC), trans-1,2-diaryl ethylene is subjected to cyclopropanation reaction with bromoform to prepare a gem-dibromocyclopropane intermediate III. The gem-dibromocyclopropane intermediate III is protonized after being subjected to bromo-lithium exchange with n-butyllithium, and a monobromocyclopropane intermediate IV is obtained. The monobromocyclopropane intermediate IV after being subjected to bromo-lithium exchange with n-butyllithium undergoes substitution reaction with $R^3R^4$PCl, and a cyclopropane skeleton monophosphine ligand I is obtained, with a reaction formula as follows:

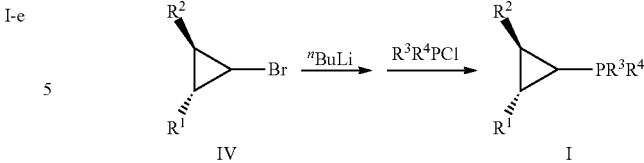

where $R^1$-$R^4$ are defined as above.

In the above technical solution, the trans-1,2-diaryl ethylene, TEBAC, and NaOH are in a molar ratio of 1:(0.1-1):(50-100); a temperature for the cyclopropanation reaction is 0° C. to room temperature; the gem-dibromocyclopropane intermediate III and n-butyllithium are in a molar ratio of 1:(1-2); the bromo-lithium exchange and protonation are performed at −120 to −60° C.; the monobromocyclopropane intermediate IV, n-butyllithium and $R^3R^4$PCl are in a molar ratio of 1:(1-2):(1-4); and the monobromocyclopropane intermediate IV, after being subjected to bromo-lithium exchange with n-butyllithium at −120-60° C., undergoes substitution reaction with $R^3R^4$PCl at −100° C. to room temperature.

When $R^5 \neq H$, a synthesis route is as follows. Iodohydrocarbon RSI is added after gem-dibromocyclopropane intermediate III is subjected to bromo-lithium exchange with n-butyllithium, to obtain an intermediate V. The intermediate V reacts with magnesium to prepare a Grignard reagent in situ, and the Grignard reagent continuously reacts with chlorodiphenylphosphine under copper catalysis to prepare a cyclopropane skeleton monophosphine ligand I, with the following reaction formula:

where $R^1$-$R^5$ are defined as above.

In the above technical solution, the gem-dibromocyclopropane intermediate III, n-butyllithium and iodoalkane RSI are in a molar ratio of 1: (1-2): (1-5); a temperature for the bromo-lithium exchange is −120° C. to room temperature; the intermediate V, magnesium, copper in the copper catalyst, and chlorodiphenylphosphine are in a molar ratio of 1:(1-10): (1-2): (1-5); the Grignard reagent is obtained in situ by the reaction of the intermediate V with magnesium at 40-90° C.; and the intermediate V continueously reacts with chlorodiphenylphosphine under copper catalysis at 40-90° C. to prepare the cyclopropane skeleton monophosphine ligand.

In another aspect of the present invention, adducts of cyclopropane skeleton monophosphine ligands and borane have the following structural formula as II or an enantiomer, a racemate of the following structural formula as II:

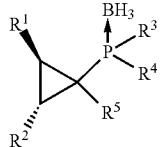

where $R^1$-$R^5$ are defined as above.

In the above technical solution, the adduct has the following structural formulas as II-a, II-b, II-c, II-d, II-e, II-f or II-g:

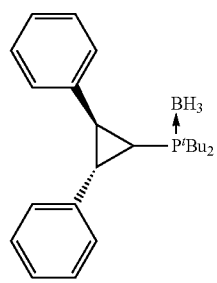

II-a

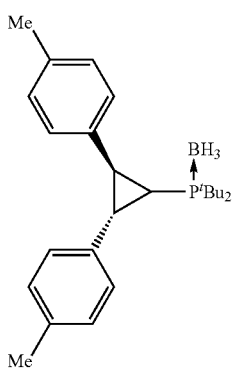

II-b

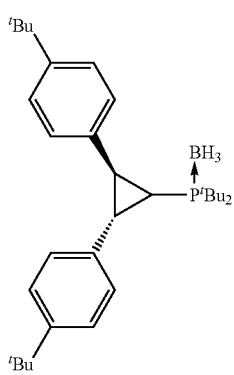

II-c

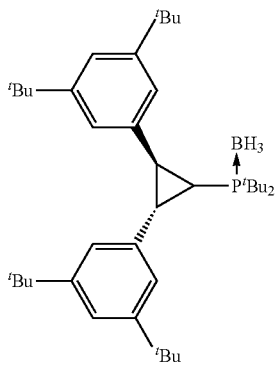

II-d

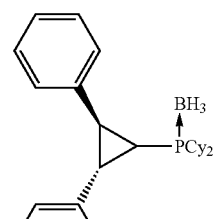

II-e

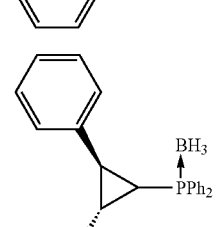

II-f

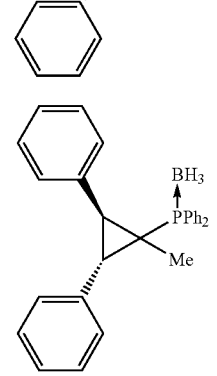

II-g

In another aspect of the present invention, a preparation method for the adducts is as follows: reacting cyclopropane skeleton monophosphine ligands with a solution of borane in tetrahydrofuran (THF) to produce corresponding adducts, with the following formula:

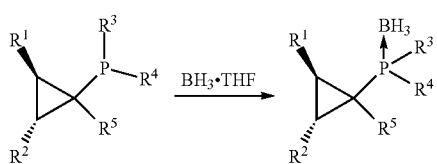

where $R^1$-$R^5$ are defined as above.

In the above technical solution, the cyclopropane skeleton monophosphine ligands and the solution of borane in THF are reacted at 0° C. to room temperature, and a reaction solvent is toluene, benzotrifluoride, benzene, THF or diethyl ether.

In another aspect of the present invention, palladium complexes of the cyclopropane skeleton monophosphine ligands have the following structural formula as VI or an enantiomer, and a racemate of VI:

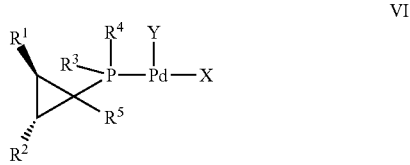

where $R^1$-$R^5$ are defined as above; and X and Y are halogen, acid anion, 1,3-dicarbonyl ligand, allyl or aryl, X and Y being same or different.

In another aspect of the present invention, synthetic methods for the palladium complexes include a method (1) or a method (2).

The method (1): reacting the cyclopropane skeleton monophosphine ligands, or adducts of the cyclopropane skeleton monophosphine ligands and borane with a palladium salt and X-Y in a solvent, followed by separation and purification to obtain the palladium complexes; and the method (2): complexing the cyclopropane skeleton monophosphine ligands, or adducts of the cyclopropane skeleton monophosphine ligands and borane with a palladium salt and X-Y in a solvent on site to obtain the palladium complexes.

The method (1) or the method (2) has the following reaction formula:

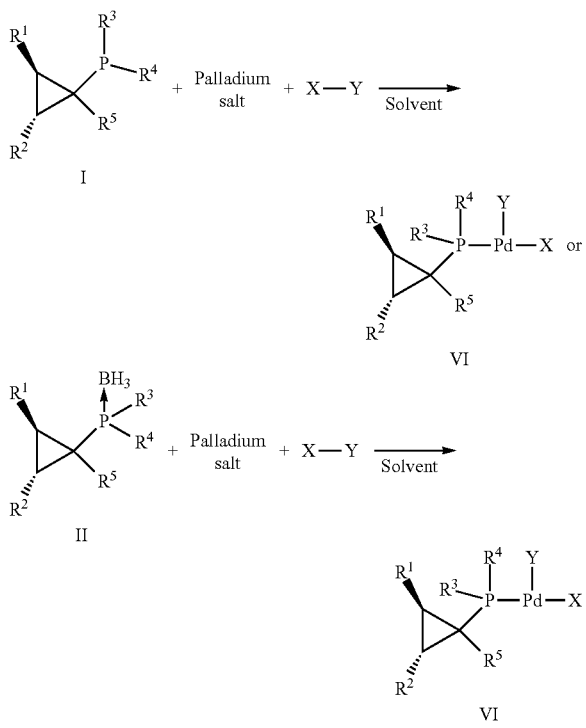

where $R^1$-$R^5$ are defined as above; the palladium salt is one or more of $(COD)Pd(CH_2TMS)_2$, $Pd_2(dba)_3 \cdot CHCl_3$, $Pd_2(dba)_4$, $Pd(OAc)_2$, $Pd(TFA)_2$ or $[(allyl)PdCl]_2$, COD being 1,5-cyclooctadiene, TMS being trimethylsilyl, dba being dibenzylideneacetone, OAc being acetate, and TFA being trifluoroacetate. Preferably, the solvent is one or more of n-hexane, THF, acetonitrile, methylene chloride, benzene, toluene, xylene or trifluoromethyl benzene.

In the above technical solution, the cyclopropane skeleton monophosphine ligand, or the adduct of cyclopropane skeleton monophosphine ligand and borane, the palladium salt and aryl halogen are in a molar ratio of 1:1: (1-5), and a reaction temperature is from 10 to 50° C.

In another aspect of the present invention, an application of palladium complexes as catalysts in promoting a Buchwald-Hartwig reaction is provided.

In the above technical solution, the palladium complexes, mixtures of the palladium complexes with the cyclopropane skeleton monophosphine ligands, or mixtures of the palladium complexes with the adducts of the cyclopropane skeleton monophosphine ligands and borane, act as catalysts to promote the Buchwald-Hartwig reaction, with the following reaction formula:

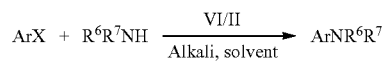

where Ar is phenyl, substituted phenyl, heteroaryl or alkenyl, X is bromine, chlorine, iodine, trifluoromethanesulfonate, nitro, or p-toluenesulfonate, and $R^6$-$R^7$ are phenyl, substituted phenyl, heteroaryl, alkenyl, alkyl, or alkyl substituted with a functional group, $R^6$ and $R^7$ being same or different. Preferably, alkali is one or more of an alkali metal salt or NaH; and a solvent is one or more of $C_1$-$C_8$ ether, toluene, alkane or a substrate itself (excluding the solvent).

In the above technical solution, the alkali metal salt is a lithium salt, a sodium salt or a potassium salt.

In the above technical solution, in the Buchwald-Hartwig reaction, the palladium complexes are synthesized before being fed into reaction systems, or, the palladium salt and the cyclopropane skeleton monophosphine ligands are fed directly into the reaction systems, to synthesize the palladium complexes in the reaction systems. In the above technical solution, when the catalyst is the palladium complex, ArX, $R^6R^7NH$, the palladium complex, and alkali are in a molar ratio of 1: (1-2): (0.001-1%): (1-3).

When the catalyst is the mixture of the palladium complex with the cyclopropane skeleton monophosphine ligand, ArX, $R^6R^7NH$, the palladium complex, the cyclopropane skeleton monophosphine ligand, and alkali are in a molar ratio of 1: (1-2): (0.001-1%): (0.001-1%): (1-3).

When the catalyst is the mixture of the palladium complex with the adduct of the cyclopropane skeleton monophosphine ligand and borane, ArX, $R^6R^7NH$, the palladium complex, the adduct of cyclopropane skeleton monophosphine ligand and borane, and alkali are in a molar ratio of 1: (1-2): (0.001-1%): (0.001-1%): (1-3).

In the above technical solution, a temperature for the Buchwald-Hartwig reaction is 50 to 200° C.

DETAILED DESCRIPTION

Figure 1:
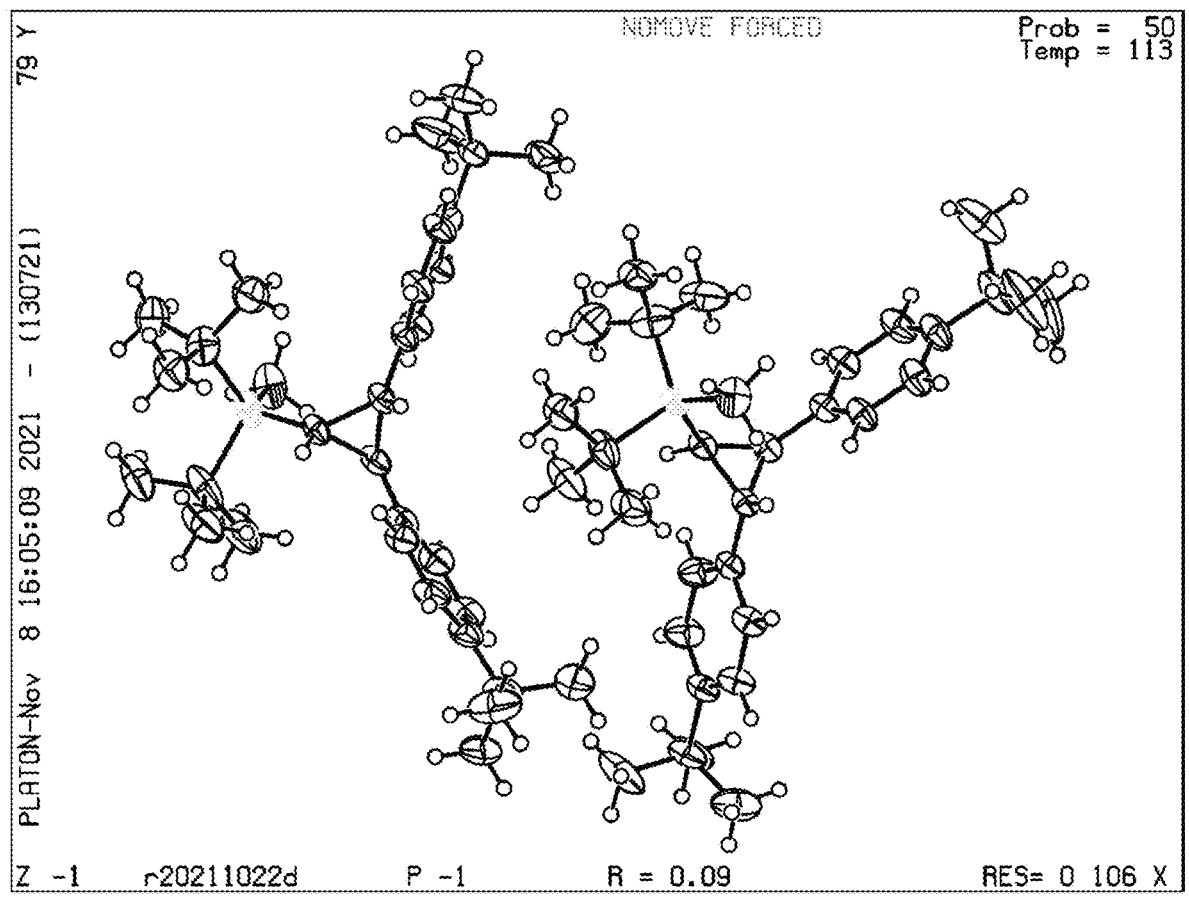
FIG. 1 shows a single-crystal structure of an adduct II-c of a cyclopropane skeleton monophosphine ligand I and borane.
Figure 2:
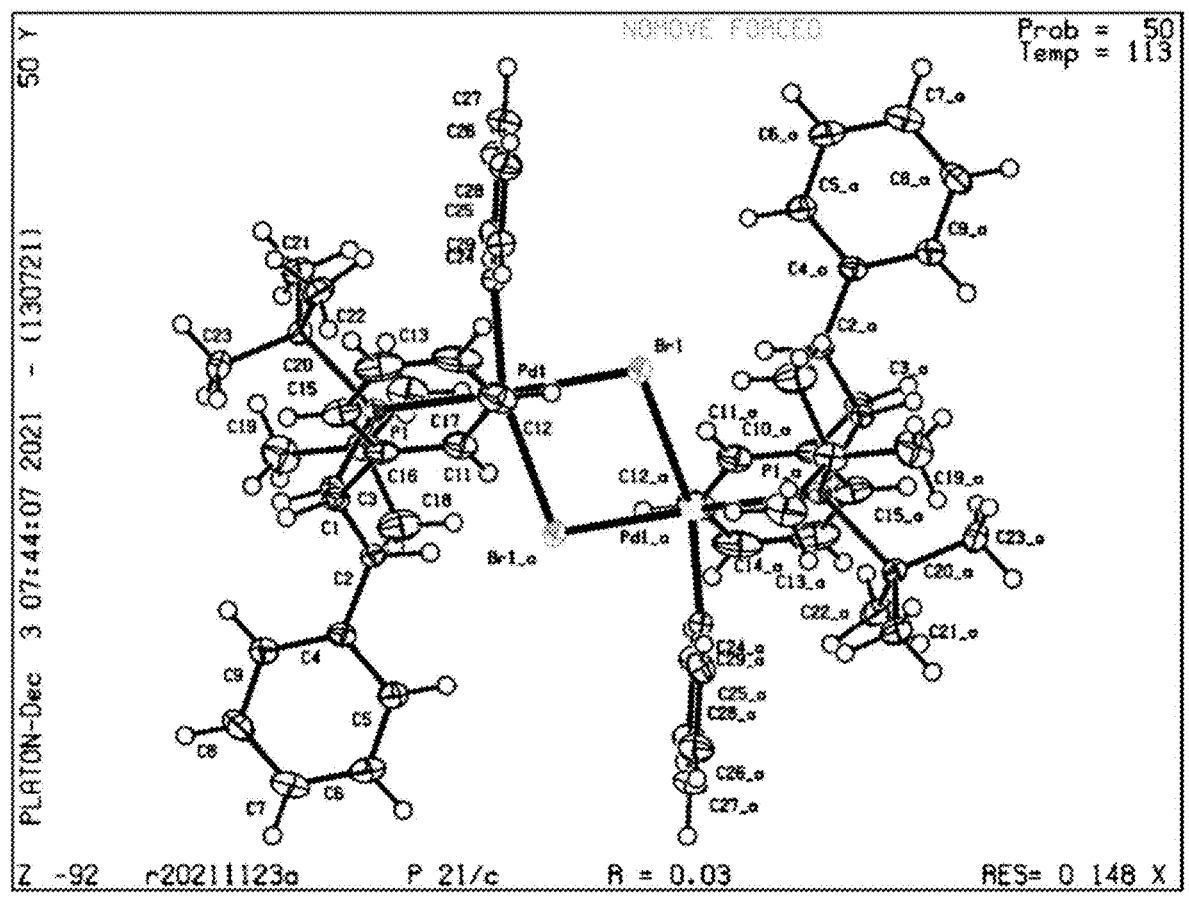
FIG. 2 shows a single-crystal structure of a palladium complex VI-h of the cyclopropane skeleton monophosphine ligand I.

The following examples help to further understand the present invention, but are not the limitation on the scope of the above-described subjects of the present invention, and any technology realized on the basis of the above-described content of the present invention is within the scope of the present invention.

General Description:

Abbreviations are used in the following examples, which have the following meanings:

Me is short for methyl, Et is short for ethyl, $^t$Bu is short for tert-butyl, $^n$Bu is short for n-butyl, Ph is short for phenyl, THF is short for tetrahydrofuran, Et$_2$O is short for diethyl ether, CHBr$_3$ is short for bromoform, TEBAC is short for benzyltriethylammonium chloride, PE is short for petroleum ether, EA is short for ethyl acetate, Ar is short for argon, CDCl$_3$ is short for deuterochloroform, COD is short for 1,5-cyclooctadiene, TMS is short for trimethylsilane substituent; dba is short for dibenzylideneacetone, OAc is short for acetate, and TFA is short for trifluoroacetate.

eq. is short for equivalent, rt is short for room temperature, TLC is short for thin layer chromatography, NMR is short for nuclear magnetic resonance, HRMS is short for high resolution mass spectrometry, GC is short for gas chromatography, turnover frequency=amount of substance of converted raw materials/amount of substance of initial raw materials, and turnover number=amount of substance of target product/amount of substance of palladium catalyst.

The solvent used is purified by standard operations and dried before use; and the reagents used are commercially available or synthesized according to existing literature methods and purified before use.

Example 1: Preparation of Trans-1,2-Diaryl-3,3-Dibromocyclopropane III-b to III-d Synthesis of trans-1,2-di-p-tolyl-3,3-dibromocyclopropane III-b

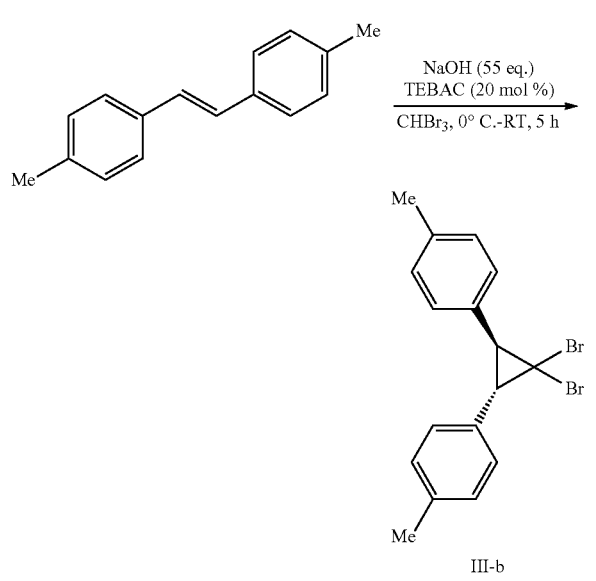

Under air, trans-1,2-di-p-tolyl ethylene (8.3 g, 40 mmol) and TEBAC (1.83 g, 8 mmol) were weighted and put into a 250 mL three-necked flask equipped with magnetic stirring, and 80 mL of CHBr$_3$ was added. NaOH (88 g, 222 mmol) was added with 80 mL of water to prepare a saturated NaOH solution, and 80 mL of saturated NaOH aqueous solution was added dropwise to the three-necked flask at 0° C., followed by stirring continuously for 20 min at 0° C. and stirring at room temperature for 5 h. The reaction was quenched by the addition of water, a liquid was separated, and an aqueous phase was extracted with dichloromethane (100 mL×3). An organic phase was washed before being dried with anhydrous Na$_2$SO$_4$. The dried organic phase was filtered, and a filtrate was concentrated by rotary evaporation, and the obtained crude product was separated by silica gel column chromatography (PE was used as an eluent) to obtain the product III-b (16.0 g, 95% yield), which was a faint yellow solid with a melting point of 55.1-56.2° C.

$^1$H NMR (400 MHZ, CDCl$_3$) δ 7.26-7.24 (m, 4H), 7.20-7.18 (m, 4H), 3.18 (s, 2H), 2.36 (s, 6H).

$^{13}$C NMR (101 MHz, CDCl$_3$) δ 137.67, 133.15, 129.26, 128.88, 39.86, 37.67, 21.37.

The following compounds (III-c to III-d) were synthesized in the same method as III-b.

trans-1,2-di-tert-butylphenyl-3,3-dibromocyclopropane III-c:

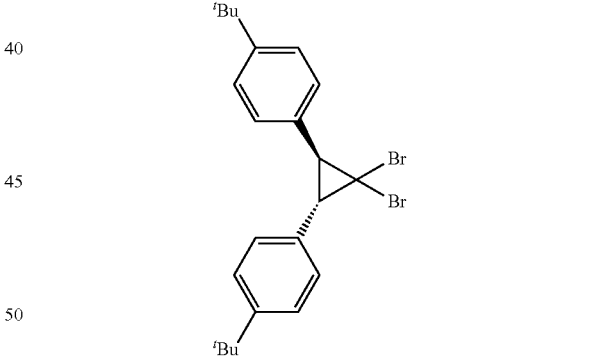

a faint yellow solid with a yield of 86% and a melting point of 119.1-120.5° C.

$^1$H NMR (400 MHZ, CDCl$_3$) δ 7.43-7.39 (m, 4H), 7.31-7.28 (m, 4H), 3.19 (s, 2H), 1.34 (s, 18H).

$^{13}$C NMR (101 MHz, CDCl$_3$) δ 150.87, 133.17, 128.68, 125.47, 39.98, 37.60, 34.76, 31.48.

trans-1,2-bis (3,5-di-tert-butylphenyl)-3,3-dibromocyclopropane III-d:

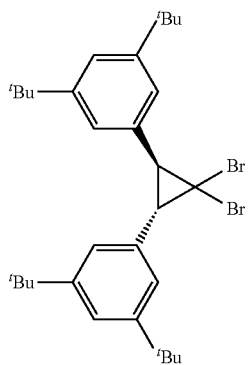

III-d a faint yellow solid with a yield of 61% and a melting point of 140.9-142.2° C.

$^1$H NMR (400 MHZ, CDCl$_3$) δ 7.43-7.39 (m, 2H), 7.23-7.20 (m, 4H), 3.26 (s, 2H), 1.38 (s, 36H).

$^{13}$C NMR (101 MHz, CDCl$_3$) δ 150.94, 135.43, 123.37, 121.76, 40.84, 37.91, 35.04, 31.64.

Example 2: Preparation of 1,2-Trans-Diaryl-3-Bromocyclopropane IV-a to IV-d

Synthesis of 1,2-trans-diphenyl-3-bromocyclopropane IV-a

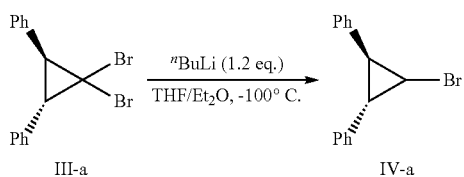 [SMILES: BrC1(Br)[C@H](c2ccccc2)[C@H]1c1ccccc1 ; BrC1[C@H](c2ccccc2)[C@H]1c1ccccc1]

under argon protection, LiBr (96 mg, 1.1 mmol), 1 mL of Et$_2$O, and 1 mL of THF were added to a 10 mL dried Schlenk tube equipped with magnetic stirring. The system was cooled to 0° C. in an ice-water bath, and a solution of $^n$BuLi in n-hexane (440 μL, 2.5 M, 1.1 mmol) was added slowly and dropwise. The system was then cooled to −100° C. using a liquid nitrogen-ethanol bath, and a solution of III-a (352 mg, 1 mmol) in THF (5 mL) was added dropwise using a syringe pump over approximately 1 h. The reaction system was quenched with methanol after being stirred at low temperature for 1 h. Water was added, and extraction was performed three times (10 mL×3) with PE. Drying was performed with anhydrous MgSO$_4$, and filtration was performed. A filtrate was concentrated by rotary evaporation, and the obtained crude product was separated by silica gel column chromatography (PE was used as an eluent) to obtain the product IV-a, which was a white solid (197 mg, 72% yield) with a melting point of 82.8-84.4° C.

$^1$H NMR (400 MHZ, CDCl$_3$) δ 7.42-7.26 (m, 8H), 7.24-7.20 (m, 2H), 3.55 (dd, J=7.9, 4.4 Hz, 1H), 2.78 (dd, J=7.0, 4.4 Hz, 1H), 2.71-2.67 (m, 1H).

$^{13}$C NMR (101 MHz, CDCl$_3$) δ 139.63, 136.64, 129.29, 128.85, 128.27, 127.22, 126.96, 126.44, 32.48, 32.14, 30.63.

The following compounds were synthesized in the same method as IV-a.

1,2-Trans-Di-p-Tolyl-3-Bromocyclopropane IV-b

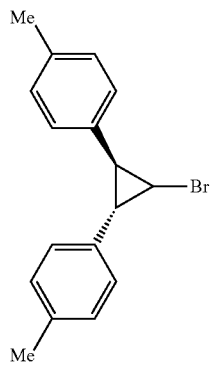

IV-b a white solid with a yield of 55% and a melting point of 74.1-75.2° C.

$^1$H NMR (400 MHZ, CDCl$_3$) δ 7.25-7.21 (m, 2H), 7.19-7.13 (m, 4H), 7.12-7.08 (m, 2H), 3.49 (dd, J=7.9, 4.3 Hz, 1H), 2.71 (dd, J=6.9, 4.3 Hz, 1H), 2.64-2.59 (m, 1H), 2.36 (s, 3H), 2.34 (s, 3H).

$^{13}$C NMR (101 MHz, CDCl$_3$) δ 139.71, 136.75, 136.65, 136.51, 135.29, 133.65, 129.45, 129.10, 128.96, 126.29, 125.76, 32.12, 31.69, 30.98, 30.80, 21.29, 21.17.

1,2-Trans-Di-p-Tert-Butylphenyl-3-Bromocyclopropane IV-c

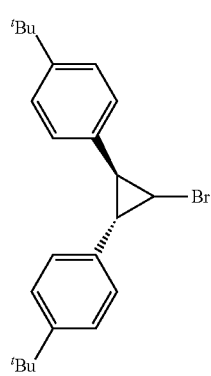

IV-c a yellow oily compound with a yield of 57%.

$^1$H NMR (400 MHZ, CDCl$_3$) δ 7.37-7.33 (m, 4H), 7.28-7.23 (m, 2H), 7.14-7.09 (m, 2H), 3.48 (dd, J=7.9, 4.4 Hz, 1H), 2.71 (dd, J=6.9, 4.4 Hz, 1H), 2.63-2.56 (m, 1H), 1.32 (s, 9H), 1.30 (s, 9H).

$^{13}$C NMR (101 MHz, CDCl$_3$) δ 149.84, 149.79, 136.76, 133.69, 128.87, 126.10, 125.68, 125.11, 34.60, 34.58, 32.33, 31.64, 31.52, 31.49, 31.40, 30.91, 27.05.

1,2-Trans-Bis(3,5-Di-Tert-Butylphenyl)-3-Bromocyclopropane IV-d

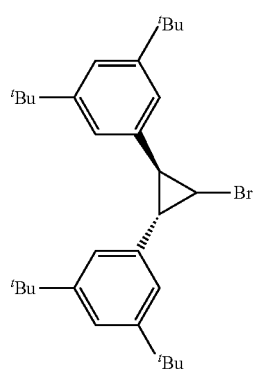

a yellow oily compound with a yield of 70%.

$^1$H NMR (400 MHZ, CDCl$_3$) δ 7.36-7.33 (m, 2H), 7.21-7.18 (m, 2H), 7.08-7.05 (m, 2H), 3.56 (dd, J=7.8, 4.5 Hz, 1H), 2.78-2.69 (m, 2H), 1.36 (s, 18H), 1.34 (s, 18H).

$^{13}$C NMR (101 MHZ, CDCl$_3$) δ 151.29, 150.38, 138.94, 135.81, 123.63, 121.16, 120.94, 120.67, 35.06, 34.98, 33.60, 32.23, 31.68, 31.65, 31.60, 31.33.

Example 3: Preparation of 2,3-Diarylcyclopropylphosphine Borane Adducts II-a to II-f Cyclopropane skeleton monophosphine ligands I-a to I-f are susceptible to oxidation, and borane adducts II-a to II-f thereof are in a stable form.

Synthesis of 2,3-Trans-Diphenylcyclopropyl Di-Tert-Butylphosphine Borane Adduct II-a

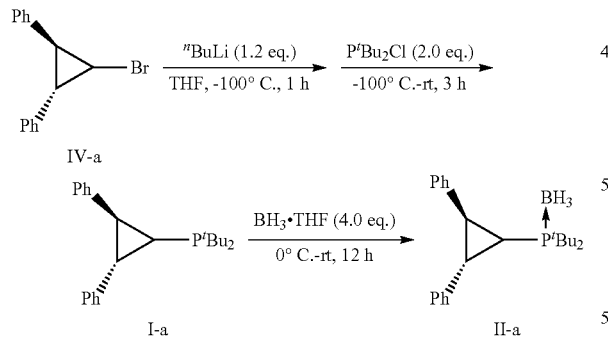

a reactant IV-a (300 mg, 1 mmol) was weighed and put into a 50 mL Schlenk flask equipped with magnetic stirring, and dissolved with anhydrous THF under argon atmosphere. A solution of $^n$BuLi in n-hexane (0.5 mL, 2.5 M, 1.2 mmol) was added dropwise at −100° C., and stirring was performed at this temperature for 1 h. Redistilled P$^t$Bu$_2$Cl (361 mg, 2 mmol) was added, and the reaction system was naturally warmed to room temperature and stirred for 4 h. After the reaction was monitored by TLC, the temperature was controlled in an ice-water bath (0° C.), a borane-THF solution (4 mL, 1.0 M, 4 mmol) was added to the system, after which the system was restored to room temperature and stirred for 12 h. The temperature was controlled in the ice-water bath, and the reaction system was quenched with water. An aqueous phase was extracted with EA (10 mL×3), and the combined organic phases were dried with anhydrous MgSO$_4$ and filtered. A filtrate was concentrated by rotary evaporation, and the obtained crude product was separated by silica gel column chromatography (eluent: PE/EA=100:1) to obtain the target product II-a (229 mg, 65% yield), which was a white solid with a melting point of 115-117° C.

$^1$H NMR (400 MHZ, CDCl$_3$) 7.45-7.40 (m, 2H), 7.36-7.30 (m, 2H), 7.29-7.19 (m, 6H), 3.25-3.16 (m, 1H), 2.85-2.77 (m, 1H), 1.68-1.61 (m, 1H), 1.19 (d, J=12.3 Hz, 9H), 1.14 (d, J=12.7 Hz, 9H).

$^{13}$C NMR (101 MHZ, CDCl$_3$) δ 140.45, 135.41, 135.39, 130.50, 128.92, 127.64, 127.08, 126.66, 125.84, 34.17, 34.12, 34.06, 33.78, 32.79, 32.52, 28.47, 28.45, 27.94, 27.93, 26.62, 22.25, 21.88.

$^{31}$P NMR (162 MHZ, CDCl$_3$) δ 47.68, 47.16.

$^{11}$B NMR (128 MHZ, CDCl$_3$) δ−42.81.

HRMS (ESI) calcd for [M+Na, C$_{23}$H34BNaP]$^+$: 375.2389, found: 375.2388.

The following compounds were synthesized in the same method as II-a.

2,3-Trans-Di-p-Tolylphenylcyclopropyl Di-Tert-Butylphosphine Borane Adduct II-b

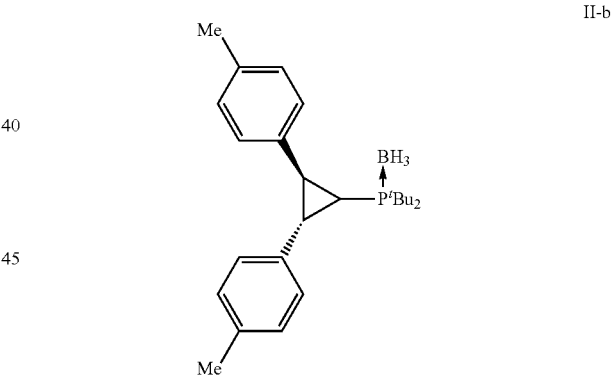

a white solid with a yield of 80% and a melting point of 174-176° C.

$^1$H NMR (400 MHZ, CDCl$_3$) δ 7.33-7.29 (m, 2H), 7.17-7.12 (m, 4H), 7.10-7.06 (m, 2H), 3.20-3.11 (m, 1H), 2.79-2.71 (m, 1H), 2.34 (s, 3H), 2.31 (s, 3H), 1.61-1.56 (m, 1H), 1.20 (d, J=12.3 Hz, 9H), 1.15 (d, J=12.7 Hz, 9H).

$^{13}$C NMR (101 MHZ, CDCl$_3$) δ 137.43, 136.47, 136.10, 132.36, 132.33, 130.30, 129.54, 128.29, 125.69, 33.99, 33.70, 32.74, 32.46, 28.51, 28.41, 27.97, 27.87, 26.37, 26.17, 21.25, 21.14.

$^{31}$P NMR (162 MHZ, CDCl$_3$) δ 47.27, 46.82.

$^{11}$B NMR (128 MHz, CDCl$_3$) δ−42.87.

HRMS (ESI) calcd for [M+Na, C$_{25}$H38BNaP]$^+$: 403.2702, found: 403.2701.

2,3-Trans-Di-p-Tert-Butylphenyl Cyclopropyl Di-Tert-Butylphosphine Borane Adduct II-c

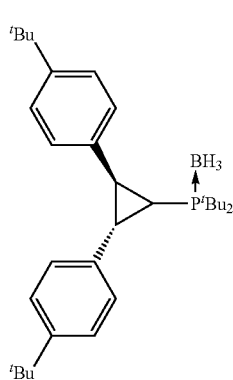

a white solid with a yield of 48% and a melting point of 200-202° C.

$^1$H NMR (400 MHZ, CDCl$_3$) δ 7.35-7.30 (m, 4H), 7.27-7.25 (m, 2H), 7.17-7.12 (m, 2H), 3.21-3.11 (m, 1H), 2.77-2.67 (m, 1H), 1.64-1.57 (m, 1H), 1.30 (s, 9H), 1.28 (s, 9H), 1.20 (d, J=12.2 Hz, 9H), 1.11 (d, J=12.7 Hz, 9H).

$^{13}$C NMR (101 MHZ, CDCl$_3$) δ 149.81, 149.36, 137.39, 132.54, 132.51, 130.01, 125.67, 125.49, 124.44, 34.52, 34.50, 33.98, 33.78, 33.73, 33.69, 32.70, 32.42, 31.48, 31.46, 28.41, 28.39, 27.99, 27.97.

$^{31}$P NMR (162 MHZ, CDCl$_3$) δ 47.43, 47.15.

$^{11}$B NMR (128 MHz, CDCl$_3$) δ−43.20.

HRMS (ESI) calcd for [M+Na, C$_{31}$H$_{50}$BNaP]$^+$: 487.3641, found: 487.3640.

2,3-Trans-Bis (3,5-Di-Tert-Butylphenyl) Cyclopropyldi-Tert-Butylphosphine Borane Adduct II-d

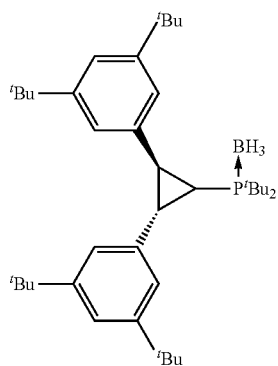

a white solid with a yield of 79% and a melting point of 195-197° C.

$^1$H NMR (400 MHZ, CDCl$_3$) δ 7.26-7.24 (m, 4H), 7.10-7.07 (m, 2H), 3.32-3.24 (m, 1H), 2.93-2.83 (m, 1H), 1.56-1.50 (m, 1H), 1.33 (s, 36H), 1.21 (d, J=12.1 Hz, 9H), 1.09 (d, J=12.7 Hz, 9H).

$^{13}$C NMR (101 MHz, CDCl$_3$) δ 151.06, 149.67, 139.35, 134.46, 134.43, 124.97, 120.74, 120.51, 120.49, 35.01, 34.94, 34.01, 33.72, 33.55, 33.50, 32.83, 32.56, 31.66, 31.66, 31.60, 28.55, 28.53, 28.00, 27.99, 26.99, 22.05, 21.68.

$^{31}$P NMR (162 MHZ, CDCl$_3$) δ 47.68.

$^{11}$B NMR (128 MHz, CDCl$_3$) δ−42.52.

HRMS (ESI) calcd for [M+Na, C$_{39}$H$_{66}$BNaP]$^+$: 599.4893, found: 599.4895.

2,3-Trans-Diphenylcyclopropyldicyclohexylphosphine Borane Adduct II-e

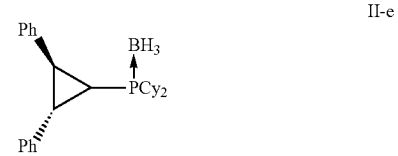

a white solid with a yield of 80% and a melting point of 82-84° C.

$^1$H NMR (400 MHZ, CDCl$_3$) δ 7.42-7.36 (m, 2H), 7.36-7.27 (m, 4H), 7.25-7.20 (m, 4H), 3.27-3.16 (m, 1H), 2.91-2.81 (m, 1H), 1.92-1.61 (m, 11H), 1.53-1.44 (m, 1H), 1.39-1.06 (m, 11H).

$^{13}$C NMR (101 MHz, CDCl$_3$) δ 140.31, 135.60, 129.84, 128.65, 127.87, 127.05, 126.49, 126.11, 99.96, 34.62, 34.28, 33.05, 32.73, 32.09, 29.68, 27.29, 27.19, 27.07, 27.00, 26.91, 26.81, 26.77, 26.24, 25.95, 21.96, 21.53.

$^{31}$P NMR (162 MHZ, CDCl$_3$) δ 29.52, 29.12.

$^{11}$B NMR (128 MHz, CDCl$_3$) δ−43.40.

HRMS (ESI) calcd for [M+Na, C$_{27}$H$_{38}$BNaP]$^+$: 427.2702, found: 427.2698.

Example 4: Preparation of 2,3-Diphenylcyclopropyl Diphenylphosphine I-f

A cyclopropane skeleton monophosphine ligand I-f is in a stable form.

Synthesis of 2,3-Trans-Diphenylcyclopropyl Di-Tert-Butylphosphine I-f

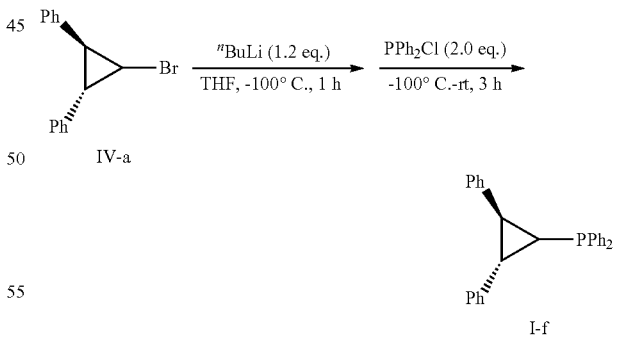

a reactant IV-a (273 mg, 1 mmol) was weighed and put into a 50 mL Schlenk flask equipped with magnetic stirring, and dissolved with anhydrous THF under argon atmosphere. A solution of $^n$BuLi in n-hexane (0.5 mL, 2.5 M, 2.5 mmol) was added dropwise at −100° C., and stirring was performed at a low temperature for 1 h. Redistilled PPh$_2$Cl (441 mg, 2 mmol) was added before the reaction system was naturally warmed up to room temperature and stirred for 4 h. The temperature of the reaction system was controlled in an ice-water bath, and the reaction system was quenched by adding water dropwise. An aqueous phase was extracted with EA (10 mL×3), the combined organic phases were dried with anhydrous MgSO$_4$ and filtered. A filtrate was concentrated by rotary evaporation, and the obtained crude product was purified by silica gel column chromatography (eluent: PE/EA=100:1). The target product I-f (303 mg, 80% yield) was obtained, which was a white solid with a melting point of 82-84° C.

$^1$H NMR (400 MHZ, CDCl$_3$) δ 7.41-7.35 (m, 2H), 7.33-7.14 (m, 18H), 2.97-2.82 (m, 2H), 2.12-2.03 (m, 1H).

$^{13}$C NMR (101 MHZ, CDCl$_3$) δ 141.29, 139.47, 139.37, 139.14, 139.04, 138.25, 138.19, 133.09, 132.90, 132.71, 132.53, 129.22, 129.19, 128.67, 128.57, 128.50, 128.44, 128.36, 128.29, 128.06, 126.65, 126.59, 126.37, 32.41, 32.35, 29.92, 29.84, 29.48, 29.35.

$^{31}$P NMR (162 MHZ, CDCl$_3$) δ−16.18.

HRMS (ESI) calcd for [M+H, C$_{41}$H35P$_2$]$^+$: 379.1616, found: 379.1615.

Example 5: Preparation of 1,2-Trans-Diphenyl-3-Bromo Gem-Methyl Cyclopropane V-a

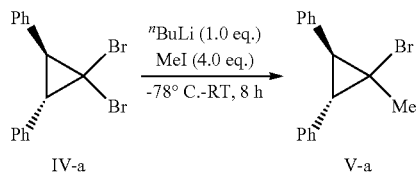 [SMILES: BrC1(Br)[C@H](c2ccccc2)[C@H]1c1ccccc1 ; CC1(Br)[C@H](c2ccccc2)[C@H]1c1ccccc1]

IV-a (2.1 g, 6 mmol) was weighed and put into a 100 mL Schlenk flask. The gas in a system was replaced with an argon atmosphere, and anhydrous THF (30 mL) was added. The system was stirred at −78° C., and $^n$BuLi (2.4 mL, 2.5 M, 6 mmol) was added dropwise, with stirring at −78° C. for 10 min. MeI (3.4 g, 24 mmol) was added dropwise in the system, and the system was continued to be stirred at −78° C. for 30 min and then warmed to room temperature and stirred for 8 h. After the reaction was completed, saturated NH$_4$Cl aqueous solution was added to quench the reaction. An aqueous phase was extracted with n-hexane (10 mL×3), and the combined organic phase was dried with anhydrous Na$_2$SO$_4$, and filtered. A filtrate was concentrated by rotary evaporation, and the obtained crude product was separated by silica gel column chromatography (eluent: PE/EA=100:1). The target product V-a (1.3 g, 74% yield) was obtained, which was a colorless oily liquid.

$^1$H NMR (400 MHZ, CDCl$_3$) δ 7.41-7.28 (m, 10H), 3.15 (d, J=7.7 Hz, 1H), 2.49 (d, J=7.7 Hz, 1H), 1.68 (s, 3H).

A cyclopropane skeleton monophosphine ligand I-g is susceptible to oxidation and a borane adduct II-g thereof is in a stable form. The preparation of 2,3-trans-diphenyl-1-methylcyclopropane diphenylphosphine borane adduct II-g is as follows:

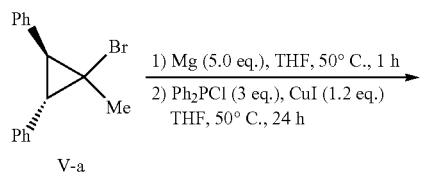

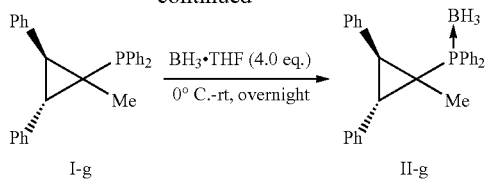

Mg crumbs (900 mg, 37.4 mmol) were weighed and put into a 50 mL three-necked round-bottomed flask, which was connected to a reflux condenser tube and a constant-pressure dropping funnel. The gas in the system was replaced with an argon atmosphere and the system was evacuated, and the system was heated and dried by a heating gun for 30 min and then filled with argon, and added with a small pellet of iodine after being returned to room temperature. Anhydrous THF (10 mL) was added, and a substrate V-a (2.15 g, 7.5 mmol) was transferred to the dropping funnel after being pre-dissolved in the anhydrous THF (5 mL). 5-10 drops of a substrate solution were added to the reaction system, and the system was heated by an air dryer to a slight boil to initiate the Grignard reaction. The rest of the substrate solution was added dropwise to keep the system in a slight boil state after the color of iodine has faded. The system was continued to be stirred at 50° C. for 30 min after the addition. CuI (1.71 g, 9 mmol) was weighed and put into another 100 mL Schlenk flask, and anhydrous THF (20 mL) was added. The prepared Grignard reagent was transferred to the Schlenk flask, and PPh$_2$Cl (4.95 g, 22.5 mmol) was added, and heating was performed for 24 h at 50° C. Subsequently, a borane-THF solution (30 mmol, 1M in THF) was added dropwise at 0° C., and the reaction was resumed at room temperature for 8 h. After the reaction, the temperature was controlled by an ice-water bath, and the reaction was quenched by adding water dropwise. An aqueous phase was extracted with EA (20 mL×3), and organic phases were combined, dried with anhydrous MgSO$_4$, and filtered. A filtrate was concentrated by rotary evaporation, and the obtained crude product was separated by silica gel column chromatography (eluent: PE/EA=100:1) to obtain the target product II-g, which was a white solid (1.98 g, 65% yield) with a melting point of 139-141° C.

$^1$H NMR (400 MHZ, CDCl$_3$) δ 7.57-7.47 (m, 4H), 7.46-7.35 (m, 6H), 7.34-7.25 (m, 5H), 7.11-6.95 (m, 5H), 3.47 (dd, J=14.4, 7.6 Hz, 1H), 2.92 (t, J=7.1 Hz, 1H), 1.25 (d, J=11.6 Hz, 3H).

$^{13}$C NMR (101 MHZ, CDCl$_3$) δ 136.3, 135.0, 133.6, 133.5, 133.4, 130.8, 130.6, 129.7, 129.4, 128.5, 128.4, 128.3, 127.8, 127.1, 126.5, 36.3, 31.0, 19.3, 19.2.

$^{31}$P NMR (162 MHZ, CDCl$_3$) δ 30.04.

$^{11}$B NMR (128 MHz, CDCl$_3$) δ−38.29.

HRMS (ESI) calcd for [M+Na, C$_{28}$H28BNaP]$^+$: 429.1914, found: 429.1916.

Example 6: Preparation of 2,3-Trans-Diphenylcyclopropyl Di-Tert-Butylphosphine I-a

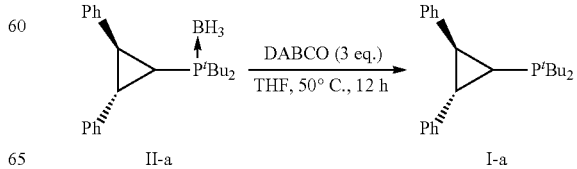

II-a (0.071 g, 0.2 mmol) and DABCO (0.067 g, 0.6 mmol) were weighed and put into a 25 mL Schlenk flask. The gas of the system was replaced with an argon atmosphere, and the system was stirred at 50° C. for 8 h after being added with anhydrous THF (4 mL). The obtained crude product was separated and purified by a silica gel column under anhydrous and anaerobic conditions to obtain the target product I-a, which was a colorless oily compound (0.064 g, 94% yield)

$^1$H NMR (400 MHZ, CDCl$_3$) δ 7.33-7.24 (m, 6H), 7.23-7.14 (m, 4H), 2.63-2.55 (m, 1H), 2.55-2.47 (m, 1H), 1.79-1.71 (m, 1H), 1.16 (d, J=10.9 Hz, 9H), 0.95 (d, J=10.8 Hz, 9H).

$^{13}$C NMR (101 MHZ, CDCl$_3$) δ 141.93, 139.73, 139.70, 128.64, 127.68, 126.06, 125.87, 125.71, 33.84, 33.81, 32.30, 32.28, 32.11, 32.09, 31.97, 31.87, 31.79, 30.45, 30.33, 30.22, 30.00, 29.92, 29.87, 29.79, 26.88, 26.80, 26.63, 26.53.

$^{31}$P NMR (162 MHz, CDCl$_3$) δ 12.88.

The following compounds were synthesized in the same method as I-a.

2,3-Trans-Di-p-Tolyl Cyclopropyl Di-Tert-Butylphosphine I-b

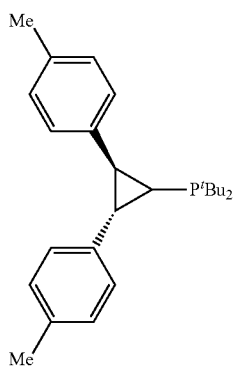

a colorless oily liquid with a yield of 95%.

$^1$H NMR (400 MHZ, CDCl$_3$) δ 7.13-7.08 (m, 2H), 7.04-6.95 (m, 6H), 2.45 (dt, J=9.1, 6.3 Hz, 1H), 2.38-2.32 (m, 1H), 2.22 (s, 3H), 2.20 (s, 3H), 1.64-1.57 (m, 1H), 1.07 (d, J=10.8 Hz, 9H), 0.88 (d, J=10.8 Hz, 9H).

$^{13}$C NMR (101 MHZ, CDCl$_3$) δ 138.97, 136.68, 136.65, 135.43, 135.18, 129.44, 129.38, 129.31, 129.26, 128.46, 128.35, 125.60, 33.38, 33.32, 32.29, 32.27, 32.11, 32.09, 31.40, 31.30, 31.20, 30.51, 30.35, 30.20, 30.07, 29.94, 29.81, 26.49, 26.26, 26.02, 21.13.

$^{31}$P NMR (162 MHZ, CDCl$_3$) δ 13.01.

2,3-Trans-Di-p-Tert-Butylphenyl Cyclopropyl Di-Tert-Butylphosphine I-c

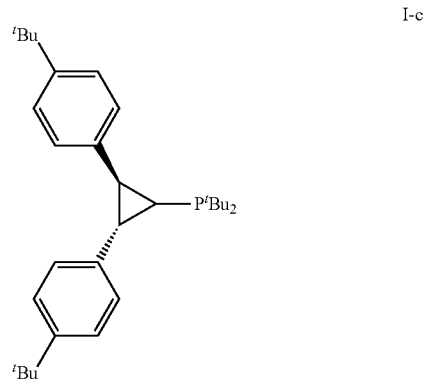

a colorless oily compound with a yield of 96%.

$^1$H NMR (400 MHZ, CDCl$_3$) δ 7.24-7.18 (m, 4H), 7.16-7.12 (m, 2H), 7.06-7.01 (m, 2H), 2.53-2.44 (m, 1H), 2.38-2.32 (m, 1H), 1.69-1.61 (m, 1H), 1.22 (s, 9H), 1.20 (s, 9H), 1.10 (d, J=10.8 Hz, 9H), 0.88 (d, J=10.8 Hz, 9H).

$^{13}$C NMR (101 MHz, CDCl$_3$) δ 148.72, 148.51, 138.91, 136.72, 136.69, 128.22, 125.58, 125.38, 124.67, 124.42, 34.49, 34.46, 33.35, 32.30, 32.28, 32.11, 31.61, 31.42, 31.26, 30.57, 30.42, 30.27, 30.03, 29.91, 29.79, 27.13, 26.01, 22.79, 14.32, 14.24.

$^{31}$P NMR (162 MHz, CDCl$_3$) δ 13.01.

2,3-Trans-Bis (3,5-Di-Tert-Butylphenyl) Cyclopropyldi-Tert-Butylphosphine I-d

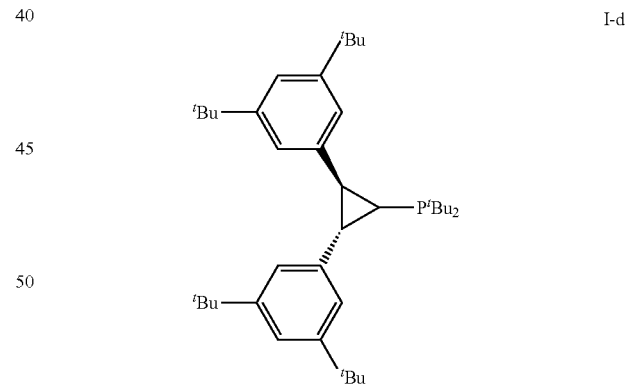

a colorless oily compound with a yield of 91%.

$^1$H NMR (400 MHZ, CDCl$_3$) δ 7.19-7.06 (m, 4H), 7.05-6.94 (m, 2H), 2.58-2.44 (m, 1H), 2.44-2.29 (m, 1H), 1.75-1.61 (m, 1H), 1.35-1.21 (m, 36H), 1.16-1.07 (m, 9H), 0.88-0.74 (m, 9H).

$^{13}$C NMR (101 MHZ, CDCl$_3$) δ 150.69, 149.51, 141.08, 139.23, 123.50, 123.32, 120.66, 120.61, 120.51, 119.87, 119.86, 119.40, 119.23, 35.03, 34.93, 34.02, 33.04, 32.28, 32.07, 31.82, 31.63, 30.64, 30.48, 30.34, 30.11, 29.99, 29.87, 25.05.

$^{31}$P NMR (162 MHZ, CDCl$_3$) δ 14.58.

2,3-Trans-Di-Phenylcyclopropyldicyclohexylphosphine I-e

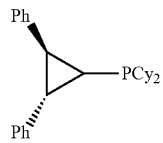

a colorless oily compound with a yield of 90%.

$^1$H NMR (400 MHz, CDCl$_3$) δ 7.25-7.17 (m, 6H), 7.13-7.05 (m, 4H), 2.53-2.43 (m, 2H), 1.73-1.35 (m, 13H), 1.22-0.97 (m, 10H).

$^{13}$C NMR (101 MHz, CDCl$_3$) δ 142.05, 139.33, 128.63, 127.69, 126.00, 33.99, 32.30, 31.01, 30.75, 30.17, 29.28, 27.45, 26.59, 26.43, 22.78, 14.30, 14.21.

$^{31}$P NMR (162 MHZ, CDCl$_3$) δ −11.30.

2,3-Trans-Di-Phenyl-1-Gem-Methylcyclopropyl Diphenylphosphine I-g

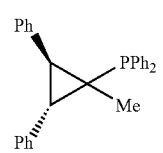

a colorless oily compound with a yield of 96%.

$^1$H NMR (400 MHZ, CDCl$_3$) δ 7.55-7.49 (m, 2H), 7.45-7.41 (m, 2H), 7.36-7.18 (m, 10H), 7.17-7.07 (m, 6H), 3.28 (dd, J=15.1, 6.7 Hz, 1H), 2.77 (dd, J=6.8, 3.7 Hz, 1H), 0.98 (d, J=2.8 Hz, 3H).

$^{13}$C NMR (101 MHZ, CDCl$_3$) δ 138.44, 138.37, 137.40, 137.37, 137.29, 137.16, 136.60, 136.46, 133.92, 133.75, 133.57, 133.33, 129.42, 129.34, 129.25, 128.43, 128.23, 128.03, 127.96, 127.93, 127.86, 126.56, 126.51, 126.45, 36.12, 36.04, 35.94, 35.87, 34.20, 34.03, 33.86, 29.34, 29.22, 17.12, 16.98.

$^{31}$P NMR (162 MHZ, CDCl$_3$) δ 7.44.

Example 7: Preparation of Palladium Complex VI-a

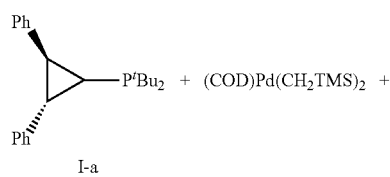

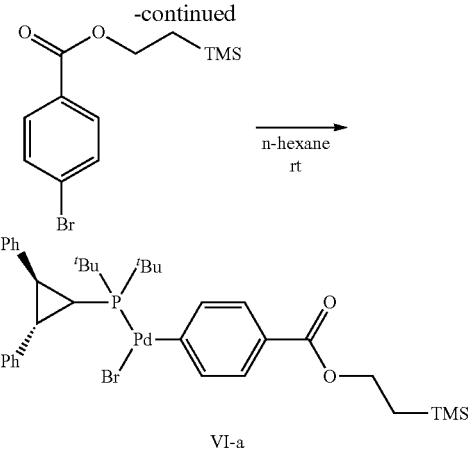

I-a (0.067 g, 0.2 mmol), (COD) Pd(CH$_2$TMS)$_2$ (0.078 g, 0.2 mmol) and 2-(trimethylsilyl) ethyl 4-bromobenzoate (0.12 g, 0.4 mmol) were weighed and put into a 25 mL Schlenk flask, and the gas in a system was replaced with an argon atmosphere, and the system was stirred at room temperature for 12 h after being added with anhydrous n-hexane (4 mL). At the end of the reaction, the system was subjected to suction filtration and washed with n-hexane to obtain the target product VI-a (0.075 g, 50% yield), which was a yellow solid with a melting point of 108.1-110.2° C.

$^1$H NMR (400 MHZ, CDCl$_3$) δ 8.24 (s, 2H), 7.76-7.27 (m, 7H), 7.18 (s, 5H), 4.36-4.26 (m, 2H), 2.79 (s, 1H), 1.75-1.40 (m, 11H), 1.11-1.02 (m, 2H), 0.77 (s, 9H), 0.05 (s, 9H).

$^{31}$P NMR (162 MHZ, CDCl$_3$) δ 44.27, 40.59.

Palladium complex VI-b:

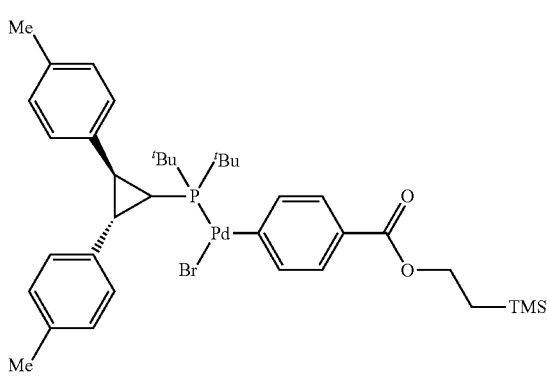

a yellow solid with a yield of 65% and a melting point of 131.0-133.3° C.

$^1$H NMR (400 MHz, CDCl$_3$) δ 8.01 (s, 2H), 7.59-7.32 (m, 5H), 7.17-6.81 (m, 5H), 4.32 (t, J=8.5 Hz, 2H), 2.69 (s, 1H), 2.45 (s, 3H), 2.32 (s, 3H), 1.87-1.35 (m, 10H), 1.28 (s, 1H), 1.08 (t, J=8.5 Hz, 2H), 0.81 (s, 9H), 0.06 (s, 9H).

$^{31}$P NMR (162 MHz, CDCl$_3$) δ 46.01, 41.24.

Palladium complex VI-c:

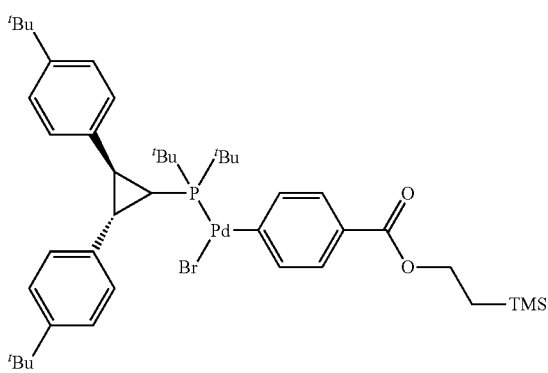

a yellow solid with a yield of 76% and a melting point of 158.1-160.0° C.

$^1$H NMR (400 MHZ, CDCl$_3$) δ 8.64-7.86 (m, 2H), 7.81-7.36 (m, 5H), 7.24 (s, 5H), 4.33 (t, J=8.4 Hz, 2H), 2.93-2.60 (m, 1H), 1.71-1.49 (m, 9H), 1.45-1.26 (m, 20H), 1.13-1.05 (m, 2H), 0.77 (s, 9H), 0.06 (s, 9H).
$^{31}$P NMR (162 MHz, CDCl$_3$) δ 43.65, 40.42, 39.03.

Palladium complex VI-d:

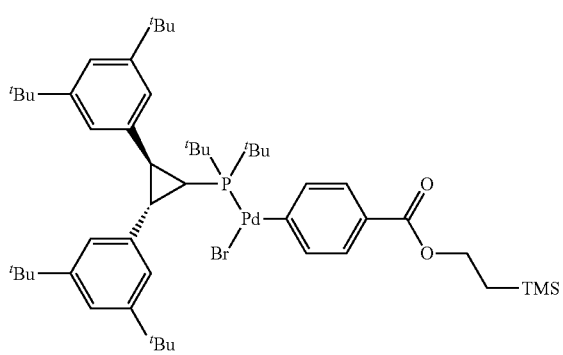

a yellow solid with a yield of 80% and a melting point of 158.2-160.5° C.

$^1$H NMR (400 MHz, CDCl$_3$) δ 7.89-7.28 (m, 7H), 7.21 (s, 1H), 7.03-6.79 (m, 2H), 4.34 (t, J=8.5 Hz, 2H), 1.62-1.40 (m, 27H), 1.38-1.20 (m, 28H), 1.11 (t, J=8.5 Hz, 4H), 0.09 (s, 9H).
$^{31}$P NMR (162 MHz, CDCl$_3$) δ 56.36, 40.28.

Palladium complex VI-e:

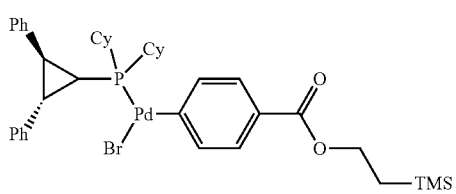

a faint yellow solid with a yield of 47% and a melting point of 140.1-142.5° C.

$^1$H NMR (400 MHZ, CDCl$_3$) δ 8.21-7.86 (m, 2H), 7.85-6.82 (m, 12H), 4.37-4.23 (m, 2H), 3.12-2.77 (m, 1H), 2.24-1.59 (m, 10H), 1.32-0.84 (m, 16H), 0.07 (s, 9H).
$^{31}$P NMR (162 MHz, CDCl$_3$) δ 29.21, 27.84, 22.23, 19.88.

Palladium complex VI-f:

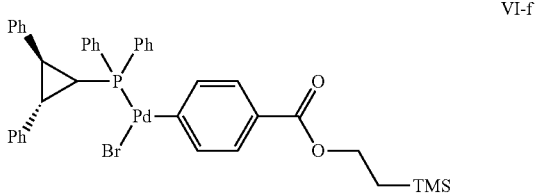

a faint yellow solid with a yield of 76% and a melting point of 126.2-128.4° C.

$^1$H NMR (400 MHZ, CDCl$_3$) δ 7.49-7.07 (m, 20H), 7.03-6.83 (m, 4H), 4.34 (s, 2H), 2.93 (s, 1H), 1.33-1.29 (m, 1H), 1.14-1.05 (m, 2H), 0.92 (t, J=6.8 Hz, 1H), 0.09 (s, 9H).
$^{31}$P NMR (162 MHz, CDCl$_3$) δ 23.00.

Palladium complex VI-g:

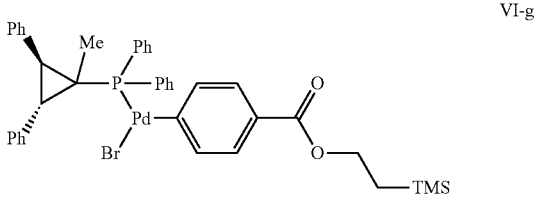

a yellow solid with a yield of 75% and a melting point of 145.0-147.5° C.

$^1$H NMR (400 MHZ, CDCl$_3$) δ 8.17-7.90 (m, 4H), 7.78-7.29 (m, 10H), 7.22-7.11 (m, 2H), 7.04-6.70 (m, 8H), 4.28 (t, J=8.3 Hz, 2H), 2.98 (t, J=7.6 Hz, 1H), 1.30 (s, 3H), 1.05 (t, J=8.2 Hz, 2H), 0.93 (s, 1H), 0.07 (s, 9H).
$^{31}$P NMR (162 MHZ, CDCl$_3$) δ 30.82, 29.89.

Example 8: Preparation of Palladium Complex VI-h

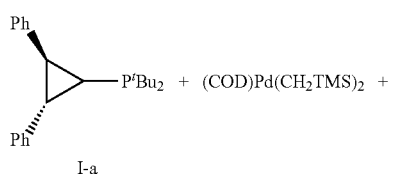

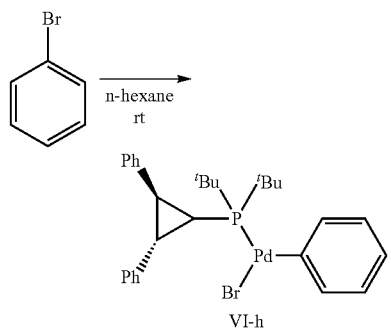

I-a (0.067 g, 0.2 mmol), (COD) Pd(CH$_2$TMS) 2 (0.078 g, 0.2 mmol) and bromobenzene (0.12 g, 0.4 mmol) were weighed and put into a 25 mL Schlenk flask, and the gas in the system was replaced with an argon atmosphere, and the system was stirred at room temperature for 12 h after being added with anhydrous n-hexane (4 mL). At the end of the reaction, the system was subjected to suction filtration and washed with n-hexane to obtain the target product VI-h (0.101 g, 83% yield), which was a yellow solid with a melting point of 161.1-162.5° C.

$^1$H NMR (400 MHZ, CDCl$_3$) δ 8.17 (s, 2H), 7.69-7.60 (m, 2H), 7.40-7.34 (m, 1H), 7.17 (s, 7H), 6.82-6.66 (m, 3H), 2.75 (dt, J=10.7, 5.8 Hz, 1H), 1.64-1.41 (m, 10H), 1.26 (s, 1H), 0.93-0.69 (m, 9H).

$^{31}$P NMR (162 MHZ, CDCl$_3$) δ 40.96, 37.30.

TABLE 1 single-crystal test parameters for II-c

| | |
|---|---|
| Empirical formula | C$_{31}$H$_{50}$BP |
| Formula weight | 464.49 |
| Temperature/K. | 113.15 |
| Crystal system | Triclinic |
| Space group | P-1 |
| a/Å | 6.6990(2) |
| b/Å | 16.1601(4) |
| c/Å | 31.1766(9) |
| α/° | 86.949(2) |
| β/° | 89.408(2) |
| γ/° | 89.936(2) |
| Volume/Å$^3$ | 3370.11(16) |
| Z | 4 |
| ρ$_{calc}$ g/cm$^3$ | 0.915 |
| μ/mm$^{-1}$ | 0.095 |
| F(000) | 1024.0 |
| Crystal size/mm$^3$ | 0.24 × 0.22 × 0.18 |
| Radiation | MoKα (λ = 0.71073) |
| 2Θ range for data collection/° | 3.538 to 52.742 |
| Index ranges | −8 ≤ h ≤ 8, −20 ≤ k ≤ 20, −38 ≤ l ≤ 38 |
| Reflections collected | 29767 |
| Independent reflections | 13595 [R$_{int}$ = 0.0573, R$_{sigma}$ = 0.0764] |
| Data/restraints/parameters | 13595/12/643 |
| Goodness-of-fit on F$^2$ | 1.024 |
| Final R indexes [I >= 2σ (I)] | R$_1$ = 0.0876, wR$_2$ = 0.2339 |
| Final R indexes [all data] | R$_1$ = 0.1195, wR$_2$ = 0.2614 |
| Largest diff. peak/hole/e Å$^{-3}$ | 0.89/−0.33 |

TABLE 2 single-crystal test parameters for palladium complex VI-h

| | |
|---|---|
| Empirical formula | C$_{29}$H$_{36}$BPPd |
| Formula weight | 601.86 |
| Temperature/K. | 113.15 |
| Crystal system | Monoclinic |
| Space group | P2$_1$/c |
| a/Å | 9.7940(3) |
| b/Å | 15.6650(4) |
| c/Å | 17.6785(5) |
| α/° | 90 |
| β/° | 101.215(3) |
| γ/° | 90 |
| Volume/Å$^3$ | 2660.50(13) |
| Z | 4 |
| ρ$_{cal}$ cg/cm$^3$ | 1.503 |

TABLE 2-continued single-crystal test parameters for palladium complex VI-h

| | |
|---|---|
| μ/mm$^{-1}$ | 2.274 |
| F(000) | 1224.0 |
| Crystal size/mm$^3$ | 0.26 × 0.24 × 0.22 |
| Radiation | MoKα (λ = 0.71073) |
| 2Θ range for data collection/° | 4.698 to 59.15 |
| Index ranges | −13 ≤ h ≤ 13, −21 ≤ h ≤ 21, −24 ≤ l ≤ 24, |
| Reflections collected | 35498 |
| Independent reflections | 7468 [R$_{int}$ = 0.0513, R$_{sigma}$ = 0.0378] |
| Data/restraints/parameters | 7468/0/296 |
| Goodness-of-fit on F$^2$ | 1.042 |
| Final R indexes [I >= 2σ (I)] | R$_1$ = 0.0330, wR$_2$ = 0.0730 |
| Final R indexes [all data] | R$_1$ = 0.0450, wR$_2$ = 0.0783 |
| Largest diff. peak/hole/e Å$^{-3}$ | 0.79/−1.07 |

Example 9: Palladium-Catalyzed C—N Bond Coupling Reactions in the Presence of Different Solvents

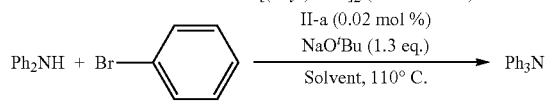

In an argon-filled glove box, diphenylamine (169 mg, 1 mmol), bromobenzene (173 mg, 1.1 mmol), sodium tert-butanolate (125 mg, 1.3 mmol), and a solvent (2 mL) were added to a 25 mL Schlenk tube, to which, 0.0183 g of [(allyl)PdCl]$_2$ toluene solution (1 mg/g) and 0.0704 g of ligand II-a toluene solution (1 mg/g) were subsequently added, and stirring was performed for 24 h after the tube was plugged with a rubber stopper. At the end of the reaction, a reaction liquid was filtered through a dropper column, and a filtrate was concentrated by rotary evaporation and added with n-tridecane as an internal standard. The yield and turnover frequency were calculated using GC.

TABLE 3 experimental results of palladium-catalyzed coupling reaction of bromobenzene with diphenylamine in the presence of different solvents

| Serial number | Solvent | Temperature (° C.) | Turnover frequency (%)$^a$ | Yield (%)$^a$ | Turnover number |
|---|---|---|---|---|---|
| 1 | PhCF$_3$ | 100 | 11 | 7 | 700 |
| 2 | Benzene | 80 | 16 | 11 | 1100 |
| 3 | Toluene | 110 | >99 | 97 | 9700 |
| 4 | O-xylene | 110 | >99 | 96 | 9600 |
| 5 | DMF | 110 | 30 | 19 | 1900 |

$^a$Turnover frequency and yield were measured by GC.

Example 10: Palladium-Catalyzed Coupling of Bromobenzene with Diphenylamine in the Presence of Different Alkali

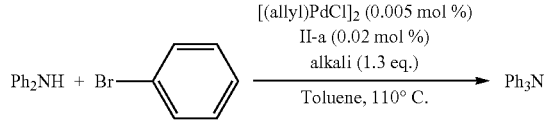

In an argon-filled glove box, diphenylamine (169 mg, 1 mmol), bromobenzene (173 mg, 1.1 mmol), alkali (1.3 mmol), and toluene (2 mL) were added to a 25 mL Schlenk tube, to which, 0.0183 g of [(allyl) PdCl]$_2$ toluene solution (1 mg/g) and 0.0704 g of ligand II-a toluene solution (1 mg/g) were subsequently added, and stirring was performed at 110° C. for 24 h after the tube was plugged with a rubber stopper. At the end of the reaction, a reaction liquid was filtered through a dropper column, and a filtrate was concentrated by rotary evaporation and added with n-tridecane as an internal standard. The yield and turnover frequency were calculated using GC.

TABLE 4 experimental results of palladium-catalyzed coupling reaction of bromobenzene with diphenylamine in the presence of different alkali

| Serial number | Alkali | Turnover frequency (%)[a] | Yield (%)[a] | Turnover number |
|---|---|---|---|---|
| 1 | NaO$^t$Bu | >99 | 98 | 9800 |
| 2 | KO$^t$Bu | 54 | 17 | 1700 |
| 3 | LiO$^t$Bu | 62 | 57 | 5700 |
| 5 | NaOEt | 9 | 7 | 700 |
| 6 | KOTMS | 25 | 24 | 2400 |
| 15 | NaH | >99 | 99 | 9900 |

[a]Turnover frequency and yield were measured by GC.

Example 11: Modulation of C—N Bond Coupling Reaction by Cyclopropane Skeleton Monophosphine Ligand-Borane Adducts in the Presence of Different Palladium Catalysts

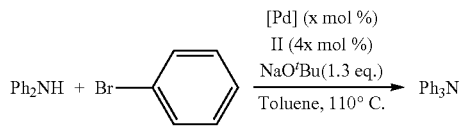

In an argon-filled glove box, diphenylamine (169 mg, 1 mmol), bromobenzene (173 mg, 1.1 mmol), sodium tert-butoxide (125 mg, 1.3 mmol), and toluene (2 mL) were added to a 25 mL Schlenk tube, to which, the prepared toluene solution (1 mg/g) of Pd and a toluene solution (1 mg/g) of ligand II were subsequently added, and stirring was performed at 110° C. for 24 h after the tube was plugged with a rubber stopper. At the end of the reaction, a reaction liquid was filtered through a dropper column, and a filtrate was concentrated by rotary evaporation and added with n-tridecane as an internal standard. The yield and turnover frequency were calculated using GC.

TABLE 5 experimental results of cyclopropane skeleton monophosphine ligand-borane adducts modulating the coupling of bromobenzene with diphenylamine in the presence of different palladium catalysts

| Serial number | [Pd] | x | II | Turnover frequency (%)[a] | Yield (%)[a] | Turnover number |
|---|---|---|---|---|---|---|
| 1 | [(allyl)PdCl]$_2$ | 0.005 | II-a | >99 | 97 | 9700 |
| 2 | [(allyl)PdCl]$_2$ | 0.0025 | II-a | 89 | 88 | 17600 |
| 3 | Pd$_2$(dba)$_3$·CHCl$_3$ | 0.0025 | II-a | 80 | 78 | 15600 |
| 4 | Pd$_2$(dba)$_4$ | 0.0025 | II-a | 81 | 80 | 16000 |
| 5 | Pd(OAc)$_2$ | 0.005 | II-a | 82 | 81 | 16200 |
| 6 | Pd(TFA)$_2$ | 0.005 | II-a | 74 | 74 | 14800 |
| 7 | VI-a | 0.005 | II-a | 93 | 93 | 18600 |
| 8[b] | VI-a | 0.005 | II-a | >99 | 97 | 19400 |
| 9[b] | VI-b | 0.005 | II-b | 96 | 95 | 19000 |
| 10[b] | VI-c | 0.005 | II-c | 91 | 90 | 18000 |
| 11[b] | VI-d | 0.005 | II-d | >99 | 97 | 19400 |
| 12[b] | VI-e | 0.005 | II-e | 91 | 90 | 18000 |
| 13[b] | VI-f | 0.005 | II-f | 48 | 45 | 9000 |
| 14[b] | VI-g | 0.005 | II-g | 55 | 51 | 10200 |
| 15[b] | VI-h | 0.005 | II-a | 85 | 80 | 16000 |
| 16[b,c] | VI-a | 0.005 | II-a | 80 | 79 | 15800 |
| 17[b] | VI-a | 0.005 | Non | 59 | 58 | 11600 |
| 18[b] | VI-a | 0.002 | II-a | 45 | 40 | 20000 |

[a]Turnover frequency and yield were measured by GC.
[b]II (2x mol %), 125° C.
[c]II (1x mol %).

Example 12: Substrate Evaluation for Palladium-Catalyzed C—N Bond Coupling Reaction

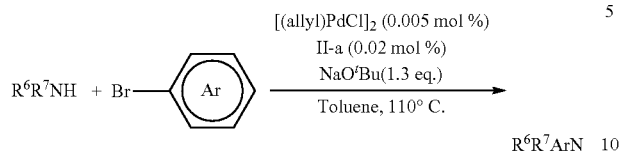

In an argon-filled glove box, secondary amine (1 mmol), a bromoaromatic compound (1.1 mmol), sodium tert-butoxide (125 mg, 1.3 mmol), and toluene (2 mL) were added to a 25 mL Schlenk tube, to which, a toluene solution of [(allyl)PdCl]$_2$ (1 mg/mL) and a toluene solution of ligand II-a (1 mg/mL) were added, and stirring was performed at 110° C. for 24 h after the tube was plugged with a rubber stopper. At the end of the reaction, the separation yield was calculated by column chromatography.

TABLE 6 substrate range for palladium-catalyzed C—N bond coupling reaction

| Serial number | Raw material | Product structure | [Pd] (%) | Yield (%)$^a$ | Turnover number | Comparative documentary record |
|---|---|---|---|---|---|---|
| 1 | Ph-NH-Ph | Ph-N(Ph)-Ph | 0.005$^c$ | 97 | 19400 | 235[1] |
| 2 | (4-MeC$_6$H$_4$)$_2$NH | (4-MeC$_6$H$_4$)$_2$NPh | 0.005$^b$ | 97 | 9700 | — |
| 3 | (4-MeOC$_6$H$_4$)$_2$NH | (4-MeOC$_6$H$_4$)$_2$NPh | 0.005$^b$ | 99 | 9900 | 90[2] |
| 4 | phenothiazine | N-phenyl phenothiazine | 0.02$^{cf}$ | 99 | 4950 | 86[3] |
| 5 | PhNH(2-MeC$_6$H$_4$) | PhN(Ph)(2-MeC$_6$H$_4$) | 0.025$^{be}$ | 90 | 1800 | — |
| 6 | (3-MeC$_6$H$_4$)(Ph)NH | bis-diarylaminobiphenyl | 0.01$^{be}$ | 91 | 4550 | 3680[4] |

TABLE 6-continued
substrate range for palladium-catalyzed C—N bond coupling reaction
| Serial number | Raw material | Product structure | [Pd] (%) | Yield (%)[a] | Turnover number | Comparative documentary record |
|---|---|---|---|---|---|---|
| 7 | 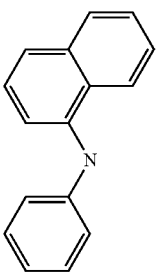 [SMILES: c1ccc(Nc2cccc3ccccc23)cc1] | 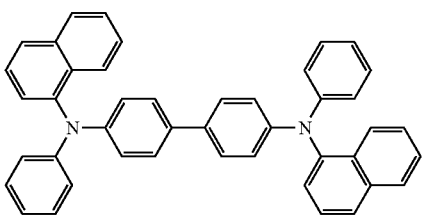 [SMILES: c1ccc(N(c2ccc(-c3ccc(N(c4ccccc4)c4cccc5ccccc45)cc3)cc2)c2cccc3ccccc23)cc1] | 0.01[be] | 99 | 4950 | 3680[4] |
| 8 | 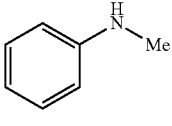 | 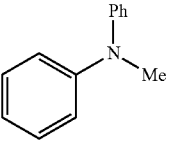 [SMILES: CN(c1ccccc1)c1ccccc1] | 0.005[ce] | 99 | 19800 | 4667[5] |
| 9 | 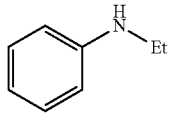 | 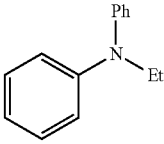 [SMILES: CCN(c1ccccc1)c1ccccc1] | 0.01[b] | 99 | 4950 | 3804[6] |
| 10 | 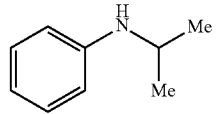 | 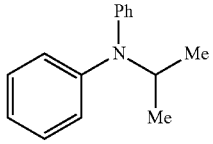 [SMILES: CC(C)N(c1ccccc1)c1ccccc1] | 0.01[bd] | 89 | 4450 | 170[7] |
| 11 | 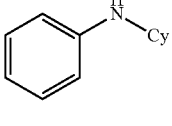 | 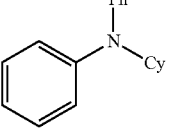 | 0.01[be] | 85 | 4250 | 172[7] |
| 12 | 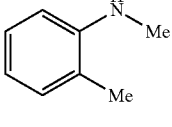 | 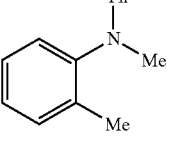 | 0.01[b] | 95 | 4750 | 38[8] |
| 13 | 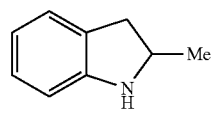 | 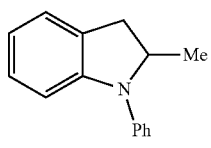 [SMILES: CC1Cc2ccccc2N1c1ccccc1] | 0.05[cf] | 99 | 1980 | 68[9] |

TABLE 6-continued substrate range for palladium-catalyzed C—N bond coupling reaction

| Serial number | Raw material | Product structure | [Pd] (%) | Yield (%)[a] | Turnover number | Comparative documentary record |
|---|---|---|---|---|---|---|
| 14 | (4-NC-C6H4)-NH-Me | (4-NC-C6H4)-N(Ph)(Me) | 0.1[c,f] | 80 | 800 | 36[10] |
| 15 | (4-MeO-C6H4)-NH-Me | (4-MeO-C6H4)-N(Ph)(Me) | 0.01[b,e] | 98 | 4900 | 45[10] |

[a]separation;
[b][(allyl)PdCl]$_2$ serves as a catalyst;
[c]Vi-a serves as a catalyst;
[d]125 °C.;
[e]150 C., 12 h, o-xylene (2 mL);
[f]180 C., 12 h, and o-xylene (2 mL).

Bibliography:
[1]Hajipour, A. R.; Dordahan, F.; Rafiee, F. *Appl. Organometal. Chem.* 2013, 27, 704.
[2]Xue, Y.-Y.; Guo, P.-P.; Yip, H.; Li, Y.; Cao, Y. *J. Mater. Chem. A.* 2017, 5, 3780.
[3]Steiner, A.; Williams, J. D.; Rincon, J. A.; Frutos, O. D.; Mateos, C. *Eur. J. Org. Chem.* 2019, 5807.
[4]Yamamoto, T.; Nishiyama, M.; Koie, Y. *Tetrahedron Lett.* 1998, 39, 2367.
[5]Silberg, J.; Schareina, T.; Kempa, R.; Wurst, K.; Buchmeiser, M. R. *J. Organomet. Chem.* 2001, 622, 6.
[6]Heshmatpour, F.; Abazari, R. *RSC Adv.* 2014, 4, 55815.
[7]Prashad, M.; Mak, X. Y.; Liu, Y.-G.; Repic, O. *J. Org. Chem.* 2003, 68, 1163.
[8]Mao, J.-Y.; Zhang, J.-D.; Zhang, S.-G.; Walsh, P. J. *Dalton Trans.* 2018, 47, 8690.
[9]Basolo, L.; Bernasconi, A.; Broggini, G.; Beccalli, E. M. *ChemSusChem* 2011, 4, 1637.
[10]Shao, Q.-L.; Jiang, Z. J.; Su, W.-K. *Tetrahedron Lett.* 2018, 59, 2277.

Example 13: Palladium-Catalyzed C—N Bond Coupling of Chlorobenzene with Diphenylamine

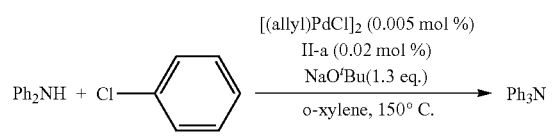

In an argon-filled glove box, diphenylamine (203 mg, 1.2 mmol), chlorobenzene (113 mg, 1 mmol), sodium tert-butanolate (125 mg, 1.3 mmol), and o-xylene (2 mL) were added to a 25 mL Schlenk tube, to which, 0.0183 g of [(allyl)PdCl]$_2$ o-xylene solution (1 mg/mL) and 0.0704 g of ligand II-a o-xylene solution (1 mg/mL) were subsequently added, and stirring was performed at 150° C. for 12 h after the tube was plugged with a rubber stopper. At the end of the reaction, a reaction liquid was filtered through a dropper column, and a filtrate was concentrated by rotary evaporation and added with n-tridecane as an internal standard. The yield and turnver number were 87% and 8700, respectively, calculated by GC.

The above are only preferred embodiments of the present invention, and it is to be noted that, for those ordinary skilled in the art, several deformations and improvements may be made without departing from the conception of the present invention, all of which fall within the scope of protection of the present invention.

The invention claimed is:

1. Cyclopropane skeleton monophosphine ligands, having the following structural formula as I:

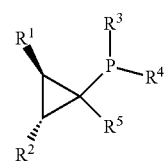

where
R$^1$ and R$^2$ are phenyl or substituted phenyl, R$^3$ and R$^4$ are C$_1$-C$_8$ alkyl, and R$^5$ is a hydrogen atom, R$^1$, R$^2$, R$^3$, R$^4$, and R$^5$ being same or different, wherein
in the substituted phenyl, a substituent is one or more of C$_1$-C$_8$ alkyl, C$_1$-C$_8$ alkoxy; if R$^1$ and R$^2$ are substituted phenyl, the number of substituents is 1 or 2.

2. The cyclopropane skeleton monophosphine ligands according to claim 1, wherein
alkyl in the C$_1$-C$_8$ alkyl or in the C$_1$-C$_8$ alkoxy is methyl, ethyl, n-propyl, isopropyl, cyclopropyl, n-butyl, isobutyl, sec-butyl, tert-butyl, n-amyl, isopentyl, neopentyl, sec-pentyl, tert-pentyl, n-hexyl, isohexyl, neohexyl, sec-hexyl, tert-hexyl, n-heptyl, isoheptyl, neoheptyl, sec-heptyl, tert-heptyl, n-octyl, isooctyl, neooctyl, sec-octyl, or tert-octyl.

3. The cyclopropane skeleton monophosphine ligands according to claim 2, having the following structural formulas as I-a, I-b, I-c or I-d:

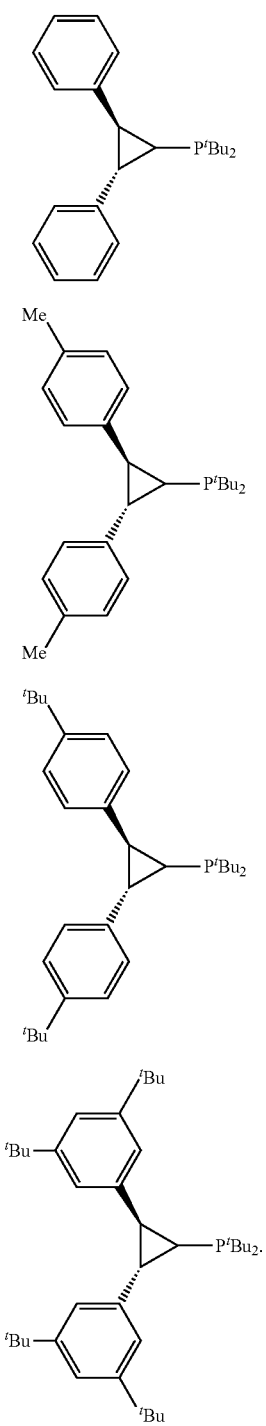

4. A preparation method for cyclopropane skeleton monophosphine ligands according to claim 1, comprising the following two routes:

when $R^5$=H, a synthetic route being as follows:
performing cyclopropanation reaction of trans-1,2-diaryl ethylene with bromoform in the presence of NaOH and a phase transfer catalyst benzyltriethylammonium chloride (TEBAC) to prepare a gem-dibromocyclopropane intermediate III;

and performing protonation of the gem-dibromocyclopropane intermediate III after being subjected to bromolithium exchange with n-butyllithium to prepare a monobromocyclopropane intermediate IV; and undergoing substitution reaction with $R^3R^4$PCl by the monobromocyclopropane intermediate IV after bromolithium exchange with n-butyllithium, to prepare a cyclopropane skeleton monophosphine ligand I, with a reaction formula as follows:

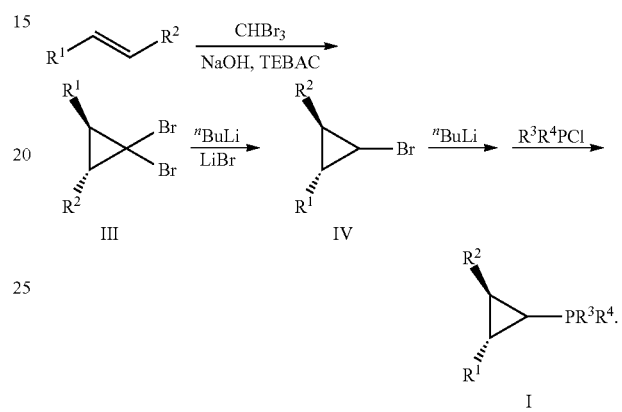

5. Adducts of cyclopropane skeleton monophosphine ligands according to claim 1 and borane, having the following structural formula as II:

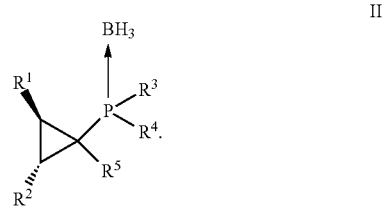

6. A preparation method for adducts according to claim 5, comprising the following steps: reacting cyclopropane skeleton monophosphine ligands with a solution of borane in tetrahydrofuran (THF) to produce corresponding adducts, with the following formula:

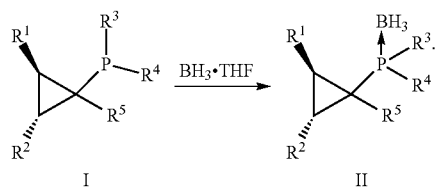

* * * * *